(12) United States Patent
Tao et al.

(10) Patent No.: US 9,006,247 B2
(45) Date of Patent: Apr. 14, 2015

(54) APOPTOSIS-INDUCING AGENTS FOR THE TREATMENT OF CANCER AND IMMUNE AND AUTOIMMUNE DISEASES

(75) Inventors: Zhi-Fu Tao, Gurnee, IL (US); Xilu Wang, Libertyville, IL (US); Andrew J. Souers, Evanston, IL (US); Nathaniel D. Catron, Vernon Hills, IL (US); Gerard M. Sullivan, Lake Villa, IL (US)

(73) Assignee: AbbVie Inc., North Chicago, IL (US)

( * ) Notice: Subject to any disclaimer, the term of this patent is extended or adjusted under 35 U.S.C. 154(b) by 601 days.

(21) Appl. No.: 13/115,376

(22) Filed: May 25, 2011

(65) Prior Publication Data

US 2012/0028925 A1  Feb. 2, 2012

Related U.S. Application Data

(60) Provisional application No. 61/348,422, filed on May 26, 2010.

(51) Int. Cl.

| A61K 31/497 | (2006.01) |
|---|---|
| C07D 401/00 | (2006.01) |
| C07F 9/02 | (2006.01) |
| A61K 31/44 | (2006.01) |
| A61K 31/18 | (2006.01) |
| C07D 471/04 | (2006.01) |

(52) U.S. Cl.
CPC ............... *A61K 31/44* (2013.01); *A61K 31/18* (2013.01); *C07D 471/04* (2013.01)

(58) Field of Classification Search
CPC ... A61K 31/497; C07D 295/04; C07D 401/12
USPC .............. 546/113; 514/253.04; 544/337, 362
See application file for complete search history.

(56) References Cited

U.S. PATENT DOCUMENTS

| 6,720,338 B2 | 4/2004 | Augeri et al. |
|---|---|---|
| 7,390,799 B2 | 6/2008 | Bruncko et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 8,426,422 B2 * | 4/2013 | Hexamer et al. ......... 514/254.09 |
| 8,546,399 B2 | 10/2013 | Bruncko et al. |
| 8,580,794 B2 | 11/2013 | Doherty et al. |
| 2007/0015787 A1 | 1/2007 | Bruncko et al. |
| 2008/0182845 A1 | 7/2008 | Bardwell et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2009/0176785 A1 | 7/2009 | Bardwell et al. |
| 2010/0152183 A1 | 6/2010 | Bruncko et al. |

FOREIGN PATENT DOCUMENTS

| WO | WO9507271 A1 | 3/1995 | |
|---|---|---|---|
| WO | WO9710223 A1 | 3/1997 | |
| WO | WO/02/24636 A2 | 3/2002 | |
| WO | WO2005049593 A2 | 6/2005 | |
| WO | WO2005049594 A1 | 6/2005 | |
| WO | WO2005099353 A2 | 10/2005 | |
| WO | WO2006008754 A1 | 1/2006 | |
| WO | 2008030836 | 3/2008 | |
| WO | WO2008124878 A1 | 10/2008 | |
| WO | WO2010/065865 * | 6/2010 | ............ 544/48 |
| WO | 2010/138588 | 12/2010 | |

OTHER PUBLICATIONS

Rega et al, "Structure-Based Discovery of a New Class of Bcl-xL Antagonists," Bioorg Chem Aug. 2007, 35(4): 344-353.

ISA/US, PCT International Search Report dated Oct. 3, 2011 for International Application No. PCT/US2011/037849.

Blagojevic, N. et al., "Role of heavy water In Boron Neutron Capture Therapy," Topics in Dosimetry & Treatment Planning for Neutron Capture Therapy, 1994, pp. 125-134.

Blake, M. I. et al., "Studies With Deuterated Drugs," Journal of Pharmaceutical Sciences, 1975, vol. 64 (3), pp. 367-391.

Brickner, S.J. et al., "Synthesis And Antibacterial Activity Of U-100592 And U-100766, Two Oxazolidinone Antibacterial Agents For The Potential Treatment Of Multidrug-Resistant Gram-Positive Bacterial Infections," Journal of Medicinal Chemistry, 1996, vol. 39 (3), pp. 673-679.

Chakrabarti A.C., et al., "Uptake of Basic Amino Acids and Peptides into Liposomes in Response to Transmembrane pH Gradients," Biophysical Journal, 1992, vol. 61 (1), pp. 228-234.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Czajka, D. M. et al., "Effect Of Deuterium Oxide On The Reproductive Potential Of Mice," Annals of the New York Academy of Sciences, 1960, vol. 84, pp. 770-779.

Czajka, D. M. et al., "Physiological Effects Of Deuterium On Dogs," American Journal of Physiology, 1961, vol. 201 (2), pp. 357-362.

Eliel, E. L. et al., "Stereochemistry of Organic Compounds," 1994, John Wiley & Sons, Inc. New York. Table of Contents.

(Continued)

*Primary Examiner* — Andrew D Kosar
*Assistant Examiner* — Raymond Convington
(74) *Attorney, Agent, or Firm* — Jones Day

(57) ABSTRACT

Disclosed are compounds which inhibit the activity of anti-apoptotic Bcl-2 proteins, compositions containing the compounds and methods of treating diseases during which is expressed anti-apoptotic Bcl-2 protein.

5 Claims, No Drawings

(56) References Cited

OTHER PUBLICATIONS

Ellens H., et al., "In Vitro Permeability Screening for Identification of Orally Bioavailable Endothelin Receptor Antagonists," Advanced Drug Delivery Reviews, 1997, vol. 23 (1-3), pp. 99-109.
Foster, A. B. et al., "Deuterium Isotope Effects in the Metabolism of Drugs and Xenobiotics: Implications for Drug Design," Advances in Drug Research, 1985, vol. 14, pp. 2-36.
Holzelova, E. et al., "Autoimmune Lymphoproliferative Syndrome with Somatic Fas Mutations," New England Journal of Medicine, 2004, vol. 351 (14), pp. 1409-1418.
Jones, C.D. et al., "Effects of Substituent Modification on Face Selection in Reduction," Journal of Organic Chemistry, 1998, vol. 63 (8), pp. 2758-2760.
Kato, S. et al., "Synthesis of Deuterated Mosapride Citrate," Journal of Labelled Compounds and Radiopharmaceuticals, 1995, vol. 36 (10), pp. 927-932.
Kushner, et al., "Pharmacological uses and perspectives of heavy water and deuterated compounds," Canadian Journal of Physiology and Pharmacology, 1999, vol. 77 (2), pp. 79-88.
Lizondo, J. et al., "Linezolid: Oxazolidinone antibacterial," Drugs of the Future, 1996, vol. 21 (11), pp. 1116-1123.
Mallesham, B. et al., "Highly Efficient Cul-Catalyzed Coupling Of Aryl Bromides With Oxazolidinones Using Buchwald's Protocol: A Short Route To Linezolid And Toloxatone," Organic Letters, 2003, vol. 5 (7), pp. 963-965.
Moore V., et al., "BCL-2 Dependence and ABT-737 Sensitivity in Acute Lymphoblastic Leukemia," Blood, 2008, vol. 111 (4), pp. 2300-2309.
Puck J.M., et al., "Immune Disorders Caused by Defects in the Caspase Cascade ," Current Allergy and Asthma Reports, 2003, vol. 3, pp. 378-384.
Rengan R., et al., "Actin Cytoskeletal Function is Spared, but Apoptosis is Increased, in WAS Patient Hematopoietic Cells," Blood, 2000, vol. 95 (4), pp. 1283-1292.
Shimazaki K., et al., "Evaluation of Apoptosis as a Prognostic Factor in Myelodysplastic Syndromes," British J Haematology, 2000, vol. 110 (3), pp. 584-590.
Sutton, V.R. et al., "Bcl-2 Prevents Apoptosis Induced By Perforin And Granzyme B, But Not That Mediated By Whole Cytotoxic Lymphocytes," Journal of Immunology, 1997, vol. 158 (12), pp. 5783-5790.
Thomson, J.F., "Physiological Effects Of $D_2O$ In Mammals," Annals of the New York Academy of Sciences, 1960, vol. 84, pp. 736-744.
Tong W.Q., Developability Assessment Supporting Drug Candidate Selection, Integrated Drug Product Development Process, University of Utah, 2006, http://www.pharmacy.utah.edu/pharmaceutics/pdf/Developability.pdf.
Tse, C. et al., "ABT-263: A Potent and Orally Bioavailable Bcl-2 Family Inhibitor," Cancer Research, 2008, vol. 68 (9), pp. 3421-3428—Including Supplementary Data.

U.S. Department of Health and Human Services Food and Drug Administration Center for Drug Evaluation and Research, Guidance for Industry, Aug. 2000, http://www.fda.gov/downloads/Drugs/GuidanceComplianceRegulatoryInformation/Guidances/ucm070246.pdf.
Wang, Z. X., "An Exact Mathematical Expression For Describing Competitive Binding Of Two Different Ligands To A Protein Molecule," FEBS Letters, 1995, vol. 360 (2), pp. 111-114.
Füllbeck M., et al., "Computer-assisted identification of small-molecule Bcl-2 modulators," Comput Biol Chem. (Dec. 2009) vol. 33, Issue 6, pp. 451-456.
Mohammad et al., "Small-Molecule Inhibitors of BcI-2 Family Proteins as Therapeutic Agents in Cancer," Recent Patents on Anti-Cancer Drug Discovery, (2008), vol. 3, No. 1, pp. 20-30.
Vogler et al., "BcI-2 inhibitors: small moledules with a big impact on cancer therapy," Cell Death and Differentiation, (2009), vol. 16, pp. 360-367.
Lessene et al.., "BCL-2 family antagonists for cancer therapy," Nature Reviews Drug Discovery, (2008), vol. 7, No. 12, pp. 989-1000.
Domling et al., "Isoteric exchange of the acylsufonamide moiey in Abbott's Bcl-XL protein interacton antagonist" Bioorganic & Medicinal Chemistry Letters, (2008), vol. 18, pp. 4115-4117.
European Patent Office, "Supplementary European Search Report for Application No. EP11787299," (Oct. 29, 2013), pp. 5.
Bardwell et al., "The Bcl-2 family antagonist ABT-737 significantlyinhibits multiple animal models ofautoimmunity, " J. immunology, 2009, vol. 182, No. 12, pp. 7482-7489.
Bruncko et al., "Studies Leading to Potent, Dual Inhibitors of Bcl-2 and Bcl-XL, " Journal of Medicinal Chemistry, 2007, vol. 50, No. 4, pp. 641-662.
Oltersdorf et al., "An inhibitor of Bcl-2 family proteins induces regression of solid tumours, " Nature, 2005, vol. 435, pp. 677-681.
Park et al., "Discovery of an Orally Bioavailable Small Molecule Inhibitor of ProsurvivalB-Cell Lymphoma 2 Proteins, " Journal of Medicinal Chemistry, 2008, vol. 51, No. 21, pp. 6902-6915.
Skoug et al., "Enabling discovery through formulation, " [slide presentation]American Association of Pharmaceutical Scientist (AAPS) Webinar, presented Mar. 18, 2010, 52 pages.
Souers et aL, "ABT-199, a potent and selective BCL-2 inhibitor, achieves antitumor activity while sparing platelets," Nature Medicine, 2013, vol. 19, pp. 202-208.
Tse et al., "ABT-263: A Potent and Orally Bioavailable Bcl-2 Family Inhibitor," Cancer Research , 2008, vol. 68, No. 9, pp. 3421-3428.
Vandenberg et al., "ABT-199, A new Bcl-2-specific BH3 mimetic,. . .," Blood, 2013, vol. 121, No. 12, pp 2285-2288.
Wendt, "Discovery of ABT-263, a Bcl-Family Protein Inhibitor: Observationson Targeting a Large-Protein Interaction, " Expert Opinion on Drug, 2008, vol. 3, No. 9, pp. 1123-1143.

\* cited by examiner

US 9,006,247 B2

APOPTOSIS-INDUCING AGENTS FOR THE TREATMENT OF CANCER AND IMMUNE AND AUTOIMMUNE DISEASES

This application claims priority to U.S. Provisional Application Ser. No. 61/348422 filed May 26, 2010, which is incorporated by reference in its entirety.

FIELD OF THE INVENTION

This invention pertains to water soluble compounds which inhibit the activity of Bcl-2 anti-apoptotic proteins, compositions containing the compounds, and methods of treating diseases during which anti-apoptotic Bcl-2 proteins are expressed.

BACKGROUND OF THE INVENTION

Anti-apoptotic Bcl-2 proteins are associated with a number of diseases. There is therefore an existing need in the therapeutic arts for compounds which inhibit the activity of anti-apoptotic Bcl-2 proteins.

Overexpression of Bcl-2 proteins correlates with resistance to chemotherapy, clinical outcome, disease progression, overall prognosis or a combination thereof in various cancers and disorders of the immune system.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110 (3), 584-90; *Blood* 2000, 95(4), 1283-92; and *New England Journal of Medicine* 2004, 351(14), 1409-1418. Involvement of Bcl-2 proteins in arthritis is disclosed in commonly-owned U.S. Provisional Patent Application Ser. No. 60/988,479. Involvement of Bcl-2 proteins in bone marrow transplant rejection is disclosed in commonly-owned U.S. patent application Ser. No. 11/941,196.

Solubility influences the oral absorption of pharmaceuticals. Drugs with poor dissolution rates are associated with low and variable bioavailability, higher potential for food effects, and inability to deliver high doses for toxicity studies, and difficulty in developing parenteral formulations. Therefore, increasing the solubility of compounds may alleviate these risks associated with low solubility and, moreover, constitute an advantage.

SUMMARY OF THE INVENTION

One embodiment of this invention, therefore, pertains to compounds or therapeutically acceptable salts, which are useful as selective inhibitors of one or more than one anti-apoptotic protein family member, the compounds having Formula (I), (II), or (III)

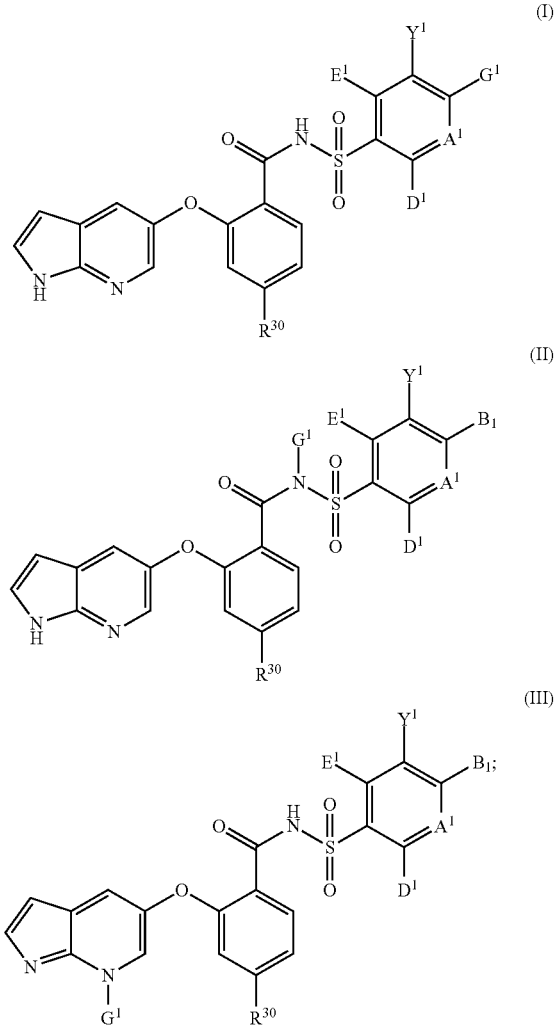

wherein
$A^4$ is N or $C(A^2)$;
$A^2$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)O$R^1$, $NR^1C(O)OR^1$, NHC(O)$NH_2$, NHC(O)NH$R^1$, NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNOR$^1$, C(O)NHSO$_2R^1$, C(NH)NH$_2$, C(NH)NHR$^1$, C(NH)N(R^1)_2$NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH_3)$, $CF_3$, C(O)OH, C(O)$NH_2$ or C(O)OR$^{1-4}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)O$R^1$, $NR^1C(O)OR^1$, NHC(O)$NH_2$, NHC(O)NH$R^1$, NHC(O)N(R^1)_2$, $NR^1C(O)NHR^1$, $NR^1C(O)N(R^1\ )_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2C(O)NHNOH$, C(O)NHNOR$^1$, C(O)NHSO$_2R^1$, C(NH)NH$_2$, C(NH)NHR$^1$, C(NH)N(R^1)_2$NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH_3)$, $CF_3$, C(O)OH, C(O)$NH_2$ or C(O)OR$^{1-4}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$;

$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$;

$G^1$ is $R^{1B}$, $OR^{1B}$, or $NHR^{1B}$;

wherein the $R^{1B}$, or a substituent on $R^{1B}$, is substituted or further substituted with $S(O)_2(OH)$, $C(O)OR^{50}OP(O)(OH)(OH)$, $C(O)R^{50}OP(O)(OH)(OH)$, $C(O)NH(R^{50})NH_2$, $C(O)R^{50}C(O)NR^{50}$; $OR^{50}P(O)(OH)(OH)$, $OP(O)(OH)(OH)$, or $OC(O)CH_2OP(O)(OH)(OH)$;

$R^1$ and $R^{1B}$ are each independently $R^2$, $R^3$, $R^4$ or $R^5$;

$R^{1A}$ is $C_1$-$C_6$-alkyl, $C_3$-$C_6$-alkenyl or $C_3$-$C_6$-alkynyl;

$R^2$ is phenyl which is unfused or fused with benzene, heteroarene or $R^{2A}$; $R^{2A}$ is cycloalkane or heterocycloalkane;

$R^3$ is heteroaryl which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is independently unsubstituted, further unsubstituted, substituted or further substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHR(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl which is unfused or fused with benzene, heteroarene or $R^{8A}$; $R^{8A}$ is cycloalkane, cycloalkene, heterocycloalkane or heterocycloalkene;

$R^9$ is heteroaryl which is unfused or fused with benzene, heteroarene or $R^{9A}$; $R^{9A}$ is cycloalkane, cycloalkene, heterocycloalkane or heterocycloalkene;

$R^{10}$ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $NHR^{12}$, $N(R^{12})_2$, $C(O)NH_2$, $C(O)NHR^{12}$, $C(O)N(R^{12})_2$, OH, (O), C(O)OH, $N_3$, CN, $NH_2$, $CF_3$, $CF_2CF_3$, F, Cl, Br or I substituents;

$R^{12}$ is $R^{13}$, $R^{14}$, $R^{15}$ or $R^{16}$;

$R^{13}$ is phenyl which is unfused or fused with benzene, heteroarene or $R^{13A}$; $R^{13A}$ is cycloalkane, cycloalkene, heterocycloalkane or heterocycloalkene;

$R^{14}$ is heteroaryl, each of which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15}A$; $R^{15A}$ is cycloalkane, cycloalkene, heterocycloalkane or heterocycloalkene;

$R^{16}$ is alkyl, alkenyl or alkynyl;

$R^{17}$ is $R^{18}$, $R^{19}$; $R^{20}$ or $R^{21}$;

$R^{18A}$ is phenyl which is unfused or fused with benzene, heteroarene or $R^{18A}$; $R^{18A}$ is cycloalkane, cycloalkene, heterocycloalkane or heterocycloalkene;

$R^{19}$ is heteroaryl which is unfused or fused with benzene, heteroarene or $R^{19A}$; $R^{19A}$ is cycloalkane, cycloalkene, heterocycloalkane or heterocycloalkene;

$R^{20}$ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three independently selected $R^{22}$, $OR^{22}$, $NHR^{22}$, $N(R^{22})_2$, $C(O)NH_2$, $C(O)NHR^{22}$, $C(O)N(R^{22})_2$, OH, (O), C(O)OH, $N_3$, CN, $NH_2$, $CF_3$, $CF_2CF_3$, F, Cl, Br or I substituents;

$R^{22}$ is $R^{23}$, $R^{24}$ or $R^{25}$;

$R^{23}$ is phenyl which is unfused or fused with benzene, heteroarene or $R^{23}A$; $R^{23A}$ is cycloalkane, cycloalkene, heterocycloalkane or heterocycloalkene;

$R^{24}$ is heteroarene which is unfused or fused with benzene, heteroarene or $R^{24A}$; $R^{24A}$ is cycloalkane, cycloalkene, heterocycloalkane or heterocycloalkene;

$R^{25}$ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{25}A$; $R^{25A}$ is cycloalkane, cycloalkene, heterocycloalkane or heterocycloalkene;

$R^{30}$ is cycloalkyl or cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{30A}$; $R^{30A}$ is cycloalkane, cycloalkene, heterocycloalkane or heterocycloalkene;

wherein $R^{30}$ is substituted with F, Cl, Br, I, $CH_2R^{37}$, $CH(R^{31})(R^{37})$, $C(R^{31})(R^{31A}(R^{37})$, $C(O)R^{37}$, $OR^{37}$, $SR^{37}$, $S(O)R^{37}$, $SO_2R^{37}$, $NHR^{37}$ or $N(R^{32})R^{37}$;

$R^{31}$ and $R^{31A}$ are independently F, Cl, Br or alkyl or are taken together and are $C_2$-$C_5$-spiroalkyl;

$R^{32}$ is $R^{33}$, $C(O)R^{33}$, or $C(O)OR^{33}$;

$R^{33}$ is $R^{34}$ or $R^{35}$;

$R^{34}$ is phenyl which is unfused or fused with benzene, heteroarene, or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)_2R^{41}$ or $SO_2R^{41}$;

$R^{38}$ is phenyl which is unfused or fused with benzene, heteroarene or $R^{38A}$; $R^{38A}$ is cycloalkane, cycloalkene, heterocycloalkane or heterocycloalkene;

$R^{39}$ is heteroaryl which is unfused or fused with benzene, heteroarene or $R^{39A}$; $R^{39A}$ is cycloalkane, cycloalkene, heterocycloalkane or heterocycloalkene;

$R^{40}$ is $C_3$-$C_8$-cycloalkyl or $C_4$-$C_8$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with benzene, heteroarene or $R^{42A}$; $R^{42A}$ is cycloalkane, cycloalkene, heterocycloalkane or heterocycloalkene;

$R^{43}$ is heteroaryl which is unfused or fused with benzene, heteroarene or $R^{43}A$; $R^{43A}$ is cycloalkane, cycloalkene, heterocycloalkane or heterocycloalkene;

$R^{44}$ is $C_3$-$C_9$-cycloalkyl or $C_4$-$C_7$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with benzene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkyl, cycloalkenyl, heterocycloalkyl or heterocycloalkenyl;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{49A}$; $R^{49A}$ is cycloalkane, cycloalkene, heterocycloalkane or heterocycloalkene;

wherein the moieties represented $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{18}$, $R^{18A}$, $R^{19}$, $R^{19A}$, $R^{20}$, $R^{20A}$, $R^{23}$, $R^{23A}$, $R^{24}$, $R^{24A}$, $R^{25}$, $R^{25A}$, $R^{30}$, $R^{30A}$, $R^{31}$ and $R^{31A}$ taken together, $R^{34}$, $R^{34A}$, $R^{36}$, $R^{36A}$, $R^{38}$, $R^{38A}$, $R^{39}$, $R^{39A}$, $R^{40}$, $R^{40A}$, $R^{42}$, $R^{42A}$, $R^{43}$, $R^{43A}$, $R^{44}$, $R^{44A}$, $R^{47}$, $R^{47A}$, $R^{48}$, $R^{48A}$, $R^{49}$, and $R^{49A}$ are independently unsubstituted, further unsubstituted, substituted or further substituted with one or two or three or four or five independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $NH_2$, $NHR^{50}$, $N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{55}SO_2R^{50}$, $SO_2NH_2$, $SO_2NHR^{50}$, $SO_2N(R^{50})_2$, $CF_3$, $CF_2CF_3$, C(O)H, C(O)OH, $C(N)NH_2$, $C(N)NHR^{50}$, $C(N)N(R^{50})_2$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl which is unfused or fused with benzene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $NHR^{55}$, $N(R^{55})_2$, $C(O)R^{55}$, $C(O)NH_2$, $C(O)NHR^{55}$, $NHC(O)R^{55}$, $NHSO_2R^{55}$, $NHC(O)OR^{55}$, $SO_2NH_2$, $SO_2NHR^{55}$, $SO_2N(R^{55})_2$, $NHC(O)NH_2$, $NHC(O)NHR^{55}$, OH, (O), C(O)OH, (O), $N_3$, CN, $NH_2$, $CF_3$, $OCF_3$, $CF_2CF_3$, $OCF_2CF_3$, F, Cl, Br or I substituents;

$R^{55}$ is alkyl, alkenyl, alkynyl, phenyl, heteroaryl or $R^{56}$;

wherein the alkyl, alkenyl, and alkynyl are unsubstituted or substituted with $OCH_3$; and $R^{56}$ is $C_3$-$C_8$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N.

In another embodiment of Formula (I), (II), or (III); $A^1$ is $C(A^2)$; and $A^2$ is H.

In another embodiment of Formula (I), (II), or (III); $A^1$ is $C(A^2)$; $A^2$ is H; and $B^1$ is $OR^1$ or $NHR^1$.

In another embodiment of Formula (I), (II), or (III); $A^1$ is $C(A^2)$; $A^2$ is H; $B^1$ is $OR^1$ or $NHR^1$; and $D^1$ is H.

In another embodiment of Formula (I), (II), or (III); $A^1$ is $C(A^2)$; $A^2$ is H; $B^1$ is $OR^1$ or $NHR^1$; $D^1$ is H; and $E^1$ is H.

In another embodiment of Formula (I), (II), or (III); $A^1$ is $C(A^2)$; $A^2$ is H; $B^1$ is $OR^1$ or $NHR^1$; $D^1$ is H; $E^1$ is H; and $Y^1$ is $NO_2$.

In another embodiment of Formula (I), (II), or (III); $A^1$ is $C(A^2)$; $A^2$ is H; $B^1$ is $OR^1$ or $NHR^1$; $D^1$ is H; $E^1$ is H; $Y^1$ is $NO_2$; and $G^1$ is $R^{1B}$, $OR^{1B}$, or $NHR^{1B}$; wherein the $R^{1B}$, or a substituent on $R^{1B}$, is substituted or further substituted with OP(O)(OH)(OH).

Still another embodiment pertains to compounds having Formula (I), (II), or (III); which are (5-{5-(4-{[2-(4-chlorophenyl)-4,4-dimethylcyclohex-1-en-1-yl]methyl}piperazin-1-yl)-2-[({3-nitro-4-[(tetrahydro-2H-pyran-4-ylmethyl)amino]phenyl}sulfonyl)carbamoyl]phenoxy}-7H-pyrrolo[2,3-b]pyridin-7-yl)methyl dihydrogen phosphate;

{5-[5-(4-{[2-(4-chlorophenyl)-4,4-dimethylcyclohex-1-en-1-yl]methyl}piperazin-1-yl)-2-{[(4-{[(trans-4-methoxycyclohexyl)methyl]amino}-3-nitrophenyl)sulfonyl]

carbamoyl}phenoxy]-7H-pyrrolo[2,3-b]pyridin-7-yl}methyl dihydrogen phosphate;

(5-{5-(4-{[2-(4-chlorophenyl)-4,4-dimethylcyclohex-1-en-1-yl]methyl}piperazin-1-yl)-2-[({4-[(4-fluorotetrahydro-2H-pyran-4-yl)methoxy]-3-nitrophenyl}sulfonyl)carbamoyl]phenoxy}-7H-pyrrolo[2,3-b]pyridin-7-yl)methyl dihydrogen phosphate;

3-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]-2,2-dimethylpropyl dihydrogen phosphate;

trans-4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenoxy)methyl]cyclohexyl dihydrogen phosphate; and therapeutically acceptable salts, and metabolites thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of a compound of Formula (I), (II), or (III).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of a compound of Formula (I), (II), or (III).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I), (II), or (III) and a therapeutically effective amount of one additional therapeutic agent or more than one additional therapeutic agent.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched hydrocarbon chain containing from 2 to 10 carbons and containing at least one carbon-carbon double bond. The term "$C_x$-$C_y$ alkyl" means a straight or branched hydrocarbon chain containing at least one carbon-carbon double bond containing x to y carbon atoms. The term "$C_3$-$C_6$ alkenyl" means an alkenyl group containing 3-6 carbon atoms. Representative examples of alkenyl include, but are not limited to, buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "$C_x$-$C_y$ alkylene" means a divalent group derived from a straight or branched hydrocarbon chain containing at least one carbon-carbon double bond and containing x to y carbon atoms. Representative examples of alkenylene include, but are not limited to, —CH═CH— and —CH$_2$CH═CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_1$-$C_6$ alkyl" means a straight or branched chain, saturated hydrocarbon containing 2 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. The term "$C_x$-$C_y$ alkylene" means a divalent group derived from a straight or branched chain, saturated hydrocarbon containing x to y carbon atoms. For example "$C_2$-$C_6$ alkylene" means a straight or branched chain, saturated hydrocarbon containing 2 to 6 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_x$-$C_y$ alkynyl" means a straight or branched chain hydrocarbon group containing from x to y carbon atoms. For example "$C_3$-$C_6$ alkynyl" means a straight or branched chain hydrocarbon group containing from 3 to 6 carbon atoms and containing at least one carbon-carbon triple bond. Representative examples of alkynyl include, but are not limited to, acetylenyl, 1-propynyl, 2-propynyl, 3-butyryl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" as used herein, means phenyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl and spiroalkyl.

The term "cycloalkylene" or cycloalkyl" or "cycloalkane" as used herein, means a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo [2.2.1 ]heptane, bicyclo [2.2.2] octane, bicyclo [3.2.1 ]octane, bicyclo[3.2.2] nonane, bicyclo[3.3.1]nonane, bicyclo[4.2.1]nonane, tricyclo[3.3.1.0$^{3,7}$]nonane(octahydro-2,5-methanopentalene or noradamantane), and tricyclo[3.3.1.1$^{3,7}$]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four to ten carbon atoms and zero heteroatoms. The four-membered ring systems have one double bond, the five- or six-membered ring systems have one or two double bonds, the seven- or eight-membered ring systems have one, two, or three double bonds, and the nine- or ten-membered rings have one, two, three, or four double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bridged cycloalkenyl groups include, but are not limited to, bicyclo[2.2.1]hept-2-ene, 4,5,6,7-tetrahydro-3aH-indene, octahydronaphthalenyl, and 1,6-dihydro-pentalene. The monocyclic and bridged cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl," or "heteroarylene," as used herein, means a five-membered or six-membered aromatic ring having at least one carbon atom and one or more than one independently selected nitrogen, oxygen or sulfur atom. The heteroarenes of this invention are connected through any adjacent atoms in the ring, provided that proper valences are maintained. Representative examples of heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl.

The term "heterocycloalkane," or "heterocycloalkyl," or "heterocycloalkylene," as used herein, means monocyclic or bridged three-, four-, five-, six-, seven-, or eight-membered ring containing at least one heteroatom independently selected from the group consisting of O, N, and S and zero double bonds. The monocyclic and bridged heterocycloalkane are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkane groups include, but are not limited to, 8-azabicyclo[3.2.1]octane, 3-azabicyclo[3.2.2]nonane, morpholinyl, tetrahydropyranyl, pyrrolidinyl, piperidinyl, dioxolanyl, tetrahydrofuranyl, thiomorpholinyl, 1,4-dioxanyl, tetrahydrothienyl, tetrahydrothiopyranyl, oxetanyl, piperazinyl, imidazolidinyl, azetidine, azepanyl, aziridinyl, diazepanyl, dithiolanyl, dithianyl, isoxazolidinyl, isothiazolidinyl, oxadiazolidinyl, oxazolidinyl, pyrazolidinyl, tetrahydrothienyl, thiadiazolidinyl, thiazolidinyl, thiomorpholinyl, trithianyl, and trithianyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of O, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkene groups include, but are not limited to, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, and thiopyranyl.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, CNOCH$_3$, S, S(O), SO$_2$ or NH and one or two CH moieties unreplaced or replaced with N.

The term "spiroheteroalkenyl," as used herein, means spiroalkenyl having one or two $CH_2$ moieties replaced with independently selected O, C(O), CNOH, CNOCH$_3$, S, S(O), SO$_2$ or NH and one or two CH moieties unreplaced or replaced with N and also means spiroalkenyl having one or two $CH_2$ moieties unreplaced or replaced with independently selected O, C(O), CNOH, CNOCH$_3$, S, S(O), SO$_2$ or NH and one or two CH moieties replaced with N.

The term, "spirocyclo," as used herein, means two substituents on the same carbon atom, that, together with the carbon atom to which they are attached, form a cycloalkane, heterocycloalkane, cycloalkene, or heterocycloalkene ring.

The term "$C_2$-$C_5$-spiroalkyl," as used herein, means $C_2$-spiroalkyl, $C_3$-spiroalkyl, $C_4$-spiroalkyl, and $C_5$-spiroalkyl.

The term "C$_2$-spiroalkyl," as used herein, means eth-1,2-ylene, both ends of which replace hydrogen atoms of the same CH$_2$ moiety.

The term "C$_3$-spiroalkyl," as used herein, means prop-1,3-ylene, both ends of which replace hydrogen atoms of the same CH$_2$ moiety.

The term "C$_4$-spiroalkyl," as used herein, means but-1,4-ylene, both ends of which replace hydrogen atoms of the same CH$_2$ moiety.

The term "C$_5$-spiroalkyl," as used herein, means pent-1,5-ylene, both ends of which replace hydrogen atoms of the same CH$_2$ moiety.

The term "C$_6$-spiroalkyl," as used herein, means hex-1,6-ylene, both ends of which replace hydrogen atoms of the same CH$_2$ moiety.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760 and E. L. Eliel, and S. H. Wilen. (1994) *Stereochemistry of Organic Compounds*. New York, N.Y.: John Wiley & Sons, Inc.

Compounds of this invention contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

One embodiment of this invention, therefore, pertains to compounds or therapeutically acceptable salts, which are useful as selective inhibitors of one or more than one anti-apoptotic protein family member, the compounds having Formula (I), (II), or (III)

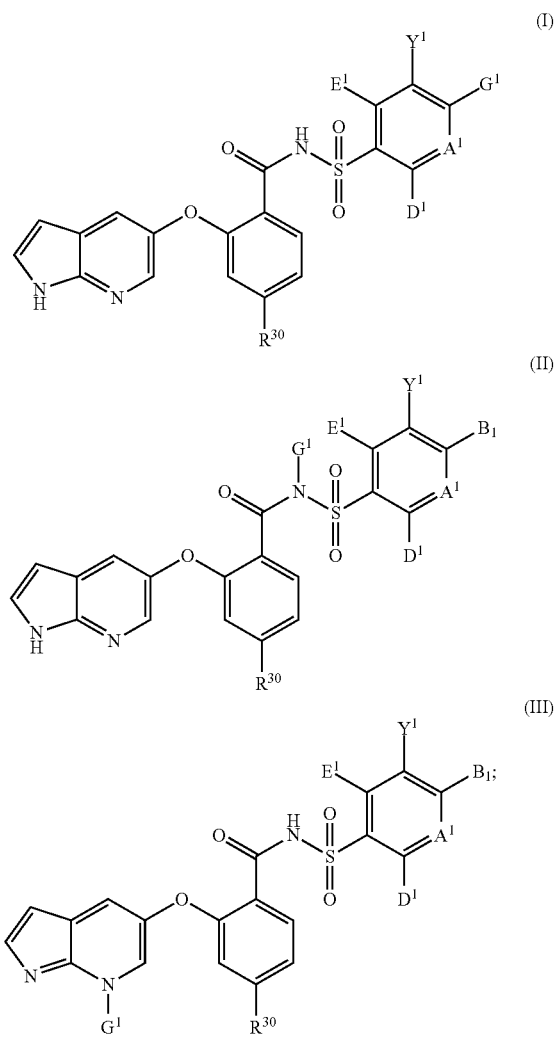

wherein
A$^1$ is N or C(A$^2$);
A$^2$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂ NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR¹ᴬ;

B¹ is H, R¹, OR¹, SR¹, S(O)R¹, SO R¹ C(O)R¹, C(O)OR¹, OC(O)R¹, NHR¹, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂ NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR¹ᴬ;

D¹ is H, R¹, OR¹, SR¹, S(O)R¹, SO₂R¹, C(O)R¹, C(O)OR¹, OC(O)R¹, NHR¹, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂ NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR¹ᴬ;

E¹ is H, R¹, OR¹, SR¹, S(O)R¹, SO₂R¹, C(O)R¹, C(O)OR¹, OC(O)R¹, NHR¹, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR¹ᴬ; and Y¹ is H, CN, NO₂, C(O)OH, F, Cl, Br, I, CF₃, OCF₃, CF₂CF₃, OCF₂CF₃, R¹⁷, OR¹⁷, C)OR¹⁷, C(O)OR¹⁷, SR¹⁷, NH₂, NHR¹⁷, N(R¹⁷)₂, NHC(O)R¹⁷, C(O)NH₂, C(O)NHR¹⁷, C(O)N(R¹⁷)₂, NHS(O)R¹⁷ or NHSO₂R¹⁷;

G¹ is R¹ᴮ, OR¹ᴮ, or NHR¹ᴮ;

wherein the R¹ᴮ, or a substituent on R¹ᴮ, is substituted or further substituted with S(O)₂(OH), C(O)OR⁵⁰OP(O)(OH)(OH), C(O)R⁵⁰OP(O)(OH)(OH), C(O)NH(R⁵⁰)NH₂, C(O)R⁵⁰C(O)NR⁵⁰; OR⁵⁰P(O)(OH)(OH), OP(O)(OH)(OH), or OC(O)CH₂OP(O)(OH)(OH);

R¹ and R¹ᴮ are each independently R², R³, R⁴ or R⁵;

R¹ᴬ is C₁-C₆-alkyl, C₃-C₆-alkenyl or C₃-C₆-alkynyl;

R² is phenyl which is unfused or fused with benzene, heteroarene or R²ᴬ; R²ᴬ is cycloalkane or heterocycloalkane;

R³ is heteroaryl which is unfused or fused with benzene, heteroarene or R³ᴬ; R³ᴬ is cycloalkane or heterocycloalkane;

R⁴ is cycloalkyl, cycloalkenyl, heterocycloalkyl or heterocycloalkenyl, each of which is unfused or fused with benzene, heteroarene or R⁴ᴬ; R⁴ᴬ is cycloalkane, cycloalkene, heterocycloalkane or heterocycloalkene;

R⁵ is alkyl, alkenyl or alkynyl, each of which is independently unsubstituted, further unsubstituted, substituted or further substituted with one or two or three independently selected R⁶, NC(R⁶ᴬ)(R⁶ᴮ), R⁷, OR⁷, SR⁷, S(O)R⁷, SO₂R⁷, NHR⁷, N(R⁷)₂, C(O)R⁷, C(O)NH₂, C(O)NHR⁷, NHC(O)R⁷, NHSO₂R⁷, NHC(O)OR⁷, SO₂NH₂, SO₂NHR⁷, SO₂N(R⁷)₂, NHC(O)NHR⁷, NHC(O)CH(CH₃)NHC(O)CH(CH₃)NH₂, NHC(O)CH(CH₃)NHC(O)CH(CH₃)NHR¹, OH, (O), C(O)OH, (O), N₃, CN, NH₂, CF₃, CF₂CF₃, F, Cl, Br or I substituents;

R⁶ is C₂-C₅-spiroalkyl, each of which is unsubstituted or substituted with OH, (O), N₃, CN, CF₃, CF₂CF₃, F, Cl, Br, I, NH₂, NH(CH₃) or N(CH₃)₂;

R⁶ᴬ and R⁶ᴮ are independently selected alkyl or, together with the N to which they are attached, R⁶ᶜ;

R⁶ᶜ is aziridin-1-yl, azetidin-1-yl, pyrrolidin-1-yl or piperidin-1-yl, each having one CH₂ moiety unreplaced or replaced with O, C(O), CNOH, CNOCH₃, S, S(O), SO₂ or NH;

R⁷ is R⁸, R⁹, R¹⁰ or R¹¹;

R⁸ is phenyl which is unfused or fused with benzene, heteroarene or R⁸ᴬ; R⁸ᴬ is cycloalkane, cycloalkene, heterocycloalkane or heterocycloalkene;

R⁹ is heteroaryl which is unfused or fused with benzene, heteroarene or R⁹ᴬ; R⁹ᴬ is cycloalkane, cycloalkene, heterocycloalkane or heterocycloalkene;

R¹⁰ is C₃-C₁₀-cycloalkyl or C₄-C₁₀-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with benzene, heteroarene or R¹⁰ᴬ; R¹⁰ᴬ is cycloalkane, cycloalkene, heterocycloalkane or heterocycloalkene;

R¹¹ is alkyl, alkenyl or alkynyl, each of which is unsubstituted or substituted with one or two or three independently selected R¹², OR¹², NHR¹², N(R¹²)₂, C(O)NH₂, C(O)NHR¹², C(O)N(R¹²)₂, OH, (O), C(O)OH, N₃, CN, NH₂, CF₃, CF₂CF₃, F, Cl, Br or I substituents;

R¹² is R¹³, R¹⁴, R¹⁵ or R¹⁶;

R¹³ is phenyl which is unfused or fused with benzene, heteroarene or R¹³ᴬ; R¹³ᴬ is cycloalkane, cycloalkene, heterocycloalkane or heterocycloalkene;

R¹⁴ is heteroaryl, each of which is unfused or fused with benzene, heteroarene or R¹⁴ᴬ; R¹⁴ᴬ is cycloalkane, cycloalkene, heterocycloalkane or heterocycloalkene;

R¹⁵ is cycloalkane, cycloalkene, heterocycloalkane or heterocycloalkene, each of which is unfused or fused with benzene, heteroarene or R¹⁵ᴬ; R¹⁵ᴬ is cycloalkane, cycloalkene, heterocycloalkane or heterocycloalkene;

R¹⁶ is alkyl, alkenyl or alkynyl;

R¹⁷ is R¹⁸, R¹⁹, R²⁰ or R²¹;

R¹⁸ is phenyl which is unfused or fused with benzene, heteroarene or R¹⁸ᴬ; R¹⁸ᴬ is cycloalkane, cycloalkene, heterocycloalkane or heterocycloalkene;

R¹⁹ is heteroaryl which is unfused or fused with benzene, heteroarene or R¹⁹ᴬ; R¹⁹ᴬ is cycloalkane, cycloalkene, heterocycloalkane or heterocycloalkene;

R²⁰ is C₃-C₁₀-cycloalkyl or C₄-C₁₀-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with benzene, heteroarene or R²⁰ᴬ; R²⁰ᴬ is cycloalkane, cycloalkene, heterocycloalkane or heterocycloalkene;

R²¹ is alkyl, alkenyl or alkynyl, each of which is unsubstituted or substituted with one or two or three independently selected R²², OR²², NHR²², N(R²²)₂, C(O)NH₂, C(O)NHR²², C(O)N(R²²)₂, OH, (O), C(O)OH, N₃, CN, NH₂, CF₃, CF₂CF₃, F, Cl, Br or I substituents;

$R^{22}$ is $R^{23}$, $R^{24}$ or $R^{25}$;

$R^{23}$ is phenyl which is unfused or fused with benzene, heteroarene or $R^{23A}$; $R^{23A}$ is cycloalkane, cycloalkene, heterocycloalkane or heterocycloalkene;

$R^{24}$ is heteroarene which is unfused or fused with benzene, heteroarene or $R^{24A}$; $R^{24A}$ is cycloalkane, cycloalkene, heterocycloalkane or heterocycloalkene;

$R^{25}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{25A}$; $R^{25A}$ is cycloalkane, cycloalkene, heterocycloalkane or heterocycloalkene;

$R^{30}$ is cycloalkyl or cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{30A}$; $R^{30A}$ is cycloalkane, cycloalkene, heterocycloalkane or heterocycloalkene;

wherein $R^{30}$ is substituted with F, Cl, Br, I, $CH_2R^{37}$, $CH(R^{31})(R^{37})$, $C(R^{31})(R^{31A})(R^{37})$, $C(O)R^{37}$, $OR^{37}$, $SR^{37}$, $S(O)R^{37}$, $SO_2R^{37}$, $NHR^{37}$ or $N(R^{32})R^{37}$;

$R^{31}$ and $R^{31A}$ are independently F, Cl, Br or alkyl or are taken together and are $C_2$-$C_5$-spiroalkyl;

$R^{32}$ is $R^{33}$, $C(O)R^{33}$, or $C(O)OR^{33}$;

$R^{33}$ is $R^{34}$ or $R^{35}$;

$R^{34}$ is phenyl which is unfused or fused with benzene, heteroarene, or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with benzene, heteroarene or $R^{38A}$; $R^{38A}$ is cycloalkane, cycloalkene, heterocycloalkane or heterocycloalkene;

$R^{39}$ is heteroaryl which is unfused or fused with benzene, heteroarene or $R^{39A}$; $R^{39A}$ is cycloalkane, cycloalkene, heterocycloalkane or heterocycloalkene;

$R^{40}$ is $C_6$-$C_8$-cycloalkyl or $C_4$-$C_8$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with benzene, heteroarene or $R^{42A}$; $R^{42A}$ is cycloalkane, cycloalkene, heterocycloalkane or heterocycloalkene;

$R^{43}$ is heteroaryl which is unfused or fused with benzene, heteroarene or $R^{43A}$; $R^{43A}$ is cycloalkane, cycloalkene, heterocycloalkane or heterocycloalkene;

$R^{44}$ is $C_3$-$C_9$-cycloalkyl or $C_4$-$C_7$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{44A}$; $R^{44}$A is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, Oh, O, $C(O)OH$, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with benzene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkyl, cycloalkenyl, heterocycloalkyl or heterocycloalkenyl;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{49A}$; $R^{49A}$ is cycloalkane, cycloalkene, heterocycloalkane or heterocycloalkene;

wherein the moieties represented by $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{18}$, $R^{18A}$, $R^{19}$, $R^{19A}$, $R^{20}$, $R^{20A}$, $R^{23}$, $R^{23A}$, $R^{24}$, $R^{24A}$, $R^{25}$, $R^{25A}$, $R^{30}$, $R^{30A}$, $R^{31}$ and $R^{31A}$ taken together, $R^{34}$, $R^{34A}$, $R^{36}$, $R^{36A}$, $R^{38}$, $R^{38A}$, $R^{39}$, $R^{39A}$, $R^{40}$, $R^{40A}$, $R^{42}$, $R^{42A}$, $R^{43}$, $R^{43A}$, $R^{44}$, $R^{44}$A, $R^{47}$, $R^{47A}$, $R^{48}$, $R^{48A}$, $R^{49}$, and $R^{49A}$ are independently unsubstituted, further unsubstituted, substituted or further substituted with one or two or three or four or five independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{55}SO_2R^{50}$, $SO_2NH_2$, $SO_2NHR^{50}$, $SO_2N(R^{50})_2$, $CF_3$, $CF_2CF_3$, $C(O)H$, $C(O)OH$, $C(N)NH_2$, $C(N)NHR^{50}$, $C(N)N(R^{50})_2$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl which is unfused or fused with benzene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $NHR^{55}$, $N(R^{55})_2$, $C(O)R^{55}$, $C(O)NH_2$, $C(O)NHR^{55}$, $NHC(O)R^{55}$, $NHSO_2R^{55}$, $NHC(O)OR^{55}$, $SO_2NH_2$, $SO_2NHR^{55}$, $SO_2N(R^{55})_2$, $NHC(O)NH_2$, $NHC(O)NHR^{55}$, OH, (O), $C(O)OH$, (O), $N_3$, CN, $NH_2$, $CF_3$, $OCF_3$, $CF_2CF_3$, $OCF_2CF_3$, F, Cl, Br or I substituents;

$R^{55}$ is alkyl, alkenyl, alkynyl, phenyl, heteroaryl or $R^{56}$;

wherein the alkyl, alkenyl, and alkynyl are unsubstituted or substituted with $OCH_3$; and $R^{56}$ is $C_3$-$C_8$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N.

In one embodiment of Formula (I), (II), or (III);

$A^1$ is $C(A^2)$;

$A^2$ is H;

$B^1$ is $OR^1$, or $NHR^1$;

$D^1$ is H;

$E^1$ is H;

Y¹ is NO₂;
G¹ is R$^{1B}$, OR$^{1B}$, or NHR$^{1B}$;
wherein the R$^{1B}$, or a substituent on R$^{1B}$, is substituted or further substituted with OP(O)(OH)(OH);
R¹ and R$^{1B}$ are each independently R⁵;
R⁵ is alkyl, which is independently further unsubstituted, or substituted with R⁷;
R⁷ is R¹⁰;
R¹⁰ is C₃-C₁₀-cycloalkyl, each having one or two CH₂ moieties unreplaced or replaced with independently selected O;
R³⁰ is cycloalkyl or cycloalkenyl, each having one or two CH moieties unreplaced or replaced with N;
wherein R³⁰ is substituted with CH₂R³⁷;
R³⁷ is R⁴⁰, each of which is substituted with R⁴¹;
R⁴⁰ is C₄-C₈-cycloalkenyl;
R⁴¹ is R⁴²;
R⁴² K is phenyl;
wherein the moieties represented by R¹⁰, R⁴⁰, and R⁴² are independently unsubstituted, further unsubstituted, substituted or further substituted with one or two or three or four or five independently selected R⁵⁰, OR⁵⁰, F, Cl, Br or I substituents;
R⁵⁰ is R⁵⁴; and
R⁵⁴ is alkyl.

In another embodiment of Formula (I), (II), or (III); A¹ is C(A²); and A² is H. In another embodiment of Formula (I), (II), or (III); A¹ is C(A²); A² is H; and B¹ is OR¹, or NHR¹. In another embodiment of Formula (I), (II), or (III); A¹ is C(A²); A² is H; B¹ is OR¹, or NHR¹; and D¹ is another embodiment of Formula (I), (II), or (III); A¹ is C(A²); A² is H; B¹ is OR¹, or NHR¹; D¹ is H; and E¹ is H. In another embodiment of Formula (I), (II), or (III); A¹ is C(A²); A² is H; B¹ is OR¹, or NHR¹; D¹ is H; E¹ is H; and Y¹ is NO₂.

In one embodiment of Formula (I), (II), or (III); G¹ is R$^{1B}$, OR$^{1B}$, or NHR$^{1B}$. In another embodiment of Formula (I), (II), or (III); A¹ is C(A²); A² is H; B¹ is OR¹, or NHR¹; D¹ is H; E¹ is H; Y¹ is NO₂; and G¹ is R$^{1B}$, OR$^{1B}$, or NHR$^{1B}$.

In one embodiment of Formula (I), (II), or (III); G¹ is R$^{1B}$, OR$^{1B}$, or NHR$^{1B}$; wherein the R$^{1B}$, or a substituent on R$^{1B}$, is substituted or further substituted with OP(O)(OH)(OH). In another embodiment of Formula (I), (II), or (III); A¹ is C(A²); A² is H; B¹ is OR¹ or NHR¹; D¹ is H; E¹ is H; Y¹ is NO₂; and G¹ is R$^{1B}$, OR$^{1B}$, or NHR$^{1B}$; wherein the R$^{1B}$, or a substituent on R$^{1B}$, is sustituted or further substituted with OP(O)(OH)(OH).

Still another embodiment pertains to compounds having Formula (I), (II) or (III) which are
(5-{5-(4-{[2-(4-chlorophenyl)-4,4-dimethylcyclohex-1-en-1-yl]methyl}piperazin-1yl)-2-[({3-nitro-4-[(tetrahydro-2H-pyran-4-ylmethyl)amino]phenyl}sulfonyl)carbamoyl]phenoxy}-7H-pyrrolo[2,3-b]pyridin-7-yl)methyl dihydrogen phosphate;
{5-[5-(4-{[2-(4-chlorophenyl)-4,4-dimethylcyclohex-1-en-1-yl]methyl}piperazin-1-yl)-2-{[(4-{[(trans-4-methoxycyclohexyl)methyl]amino}-3-nitrophenyl)sulfonyl]carbamoyl}phenoxy]-7H-pyrrolo[2,3-b]pyridin-7-yl}methyl dihydrogen phosphate;
(5-{5-(4-{[2-(4-chlorophenyl)-4,4-dimethylcyclohex-1-en-1-yl]methyl}piperazin-1-yl)-2-[({4-[(4-fluorotetrahydro-2H-pyran-4-yl)methoxy]-3-nitrophenyl}sulfonyl)carbamoyl]phenoxy}-7H-pyrrolo[2,3-b]pyridin-7-yl)methyl dihydrogen phosphate;
3-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]-2,2-dimethylpropyl dihydrogen phosphate;
trans-4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenoxy)methyl]cyclohexyl dihydrogen phosphate; and
therapeutically acceptable salts, and metabolites thereof.

One embodiment of this invention, therefore, pertains to compounds or therapeutically acceptable salts, which are useful as selective inhibitors of one or more than one anti-apoptotic protein family member, the compounds having Formula (I)

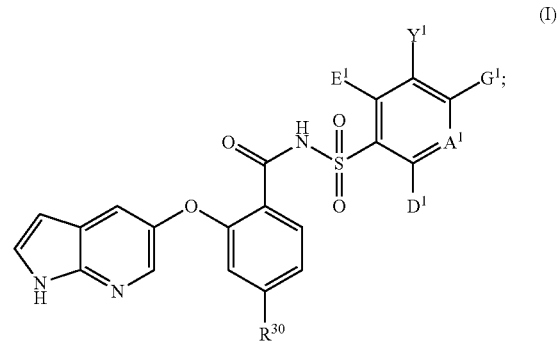

wherein
A¹ is N or C(A²);
A² is H, R¹, OR¹, SR¹, S(O)R¹, SO₂R¹ C(O)R¹, C(O)OR¹, OC(O)R¹, NHR¹N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂ NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR$^{1A}$;
D¹ is H, R¹, OR¹, SR¹, S(O)R¹, SO₂R¹, C(O)R¹, C(O)OR¹, OC(O)R¹, NHR¹, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR$^{1A}$;
E¹ is H, R¹, OR¹, SR¹, S(O)R¹, SO₂R¹, C(O)R¹, C(O)OR¹, OC(O)R¹, NHR¹, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR$^{1A}$; and
Y¹ is H, CN, NO₂, C(O)OH, F, Cl, Br, I, CF₃, OCF₃, CF₂CF₃, OCF₂CF₃, R¹⁷, OR¹⁷, C(O)R¹⁷, C(O)OR¹⁷, SR¹⁷, NH$_2$, NHR$^{17}$, N(R$^{17}$)$_2$, NHC(O)R$^{17}$, C(O)NH$_2$, C(O)NHR$^{17}$, C(O)N(R$^{17}$)$_2$, NHS(O)R$^{17}$ or NHSO$_2$R$^{17}$;

G$^1$ is R$^{1B}$, OR$^{1B}$, or NHR$^{1B}$;

wherein the R$^{1B}$, or a substituent on R$^{1B}$, is substituted or further substituted with S(O)$_2$(OH), C(O)OR$^{50}$OP(O)(OH)(OH), C(O)R$^{50}$OP(O)(OH)(OH), C(O)NH(R$^{50}$)NH$_2$, C(O)R$^{50}$C(O)NR$^{50}$; OR$^{50}$P(O)(OH)(OH), OP(O)(OH)(OH), or OC(O)CH$_2$OP(O)(OH)(OH);

R$^1$ and R$^{1B}$ are each independently R$^2$, R$^3$, R$^4$ or R$^5$;

R$^{1A}$ is C$_1$-C$_6$-alkyl, C$_3$-C$_6$-alkenyl or C$_3$-C$_6$-alkynyl;

R$^2$ is phenyl which is unfused or fused with benzene, heteroarene or R$^{2A}$; R$^{2A}$ is cycloalkane or heterocycloalkane;

R$^3$ is heteroaryl which is unfused or fused with benzene, heteroarene or R$^{3A}$; R$^{3A}$ is cycloalkane or heterocycloalkane;

R$^4$ is cycloalkyl, cycloalkenyl, heterocycloalkyl or heterocycloalkenyl, each of which is unfused or fused with benzene, heteroarene or R$^{4A}$; R$^{4A}$ is cycloalkane, cycloalkene, heterocycloalkane or heterocycloalkene;

R$^5$ is alkyl, alkenyl or alkynyl, each of which is independently unsubstituted, further unsubstituted, substituted or further substituted with one or two or three independently selected R$^6$, NC(R$^{6A}$)(R$^{6B}$), R$^7$, OR$^7$, SR$^7$, S(O)R$^7$, SO$_2$R$^7$, NHR$^7$, N(R$^7$)$_2$, C(O)R$^7$, C(O)NHR$^7$, NHC(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, NHC(O)CH(CH$_3$)NHC(O)CH(CH$_3$)NHR$^1$, OH, (O), C(O)OH, (O), N$_3$, CN, NH$_2$, CF$_3$, CF$_2$CF$_3$, F, Cl, Br or I substituents;

R$^6$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^7$ is R$^8$, R$^9$, R$^{10}$ or R$^{11}$;

R$^8$ is phenyl which is unfused or fused with benzene, heteroarene or R$^{8A}$; R$^{8A}$ is cycloalkane, cycloalkene, heterocycloalkane or heterocycloalkene;

R$^9$ is heteroaryl which is unfused or fused with benzene, heteroarene or R$^{9A}$; R$^{9A}$ is cycloalkane, cycloalkene, heterocycloalkane or heterocycloalkene;

R$^{10}$ is C$_3$-C$_{10}$-cycloalkyl or C$_4$-C$_{10}$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{10A}$; R$^{10A}$ is cycloalkane, cycloalkene, heterocycloalkane or heterocycloalkene;

R$^{11}$ is alkyl, alkenyl or alkynyl, each of which is unsubstituted or substituted with one or two or three independently selected R$^{12}$, OR$^{12}$, NHR$^{12}$, N(R$^{12}$)$_2$, C(O)NH$_2$, C(O)NHR$^{12}$, C(O)N(R$^{12}$)$_2$, OH, (O), C(O)OH, N$_3$, CN, NH$_2$, CF$_3$, CF$_2$CF$_3$, F, Cl, Br or I substituents;

R$^{12}$ is R$^{13}$, R$^{14}$, R$^{15}$ or R$^{16}$;

R$^{13}$ is phenyl which is unfused or fused with benzene, heteroarene or R$^{13A}$; R$^{13A}$ is cycloalkane, cycloalkene, heterocycloalkane or heterocycloalkene;

R$^{14}$ is heteroaryl, each of which is unfused or fused with benzene, heteroarene or R$^{14A}$; R$^{14A}$ is cycloalkane, cycloalkene, heterocycloalkane or heterocycloalkene;

R$^{15}$ is cycloalkane, cycloalkene, heterocycloalkane or heterocycloalkene, each of which is unfused or fused with benzene, heteroarene or R$^{15A}$; R$^{15A}$ is cycloalkane, cycloalkene, heterocycloalkane or heterocycloalkene;

R$^{16}$ is alkyl, alkenyl or alkynyl;

R$^{17}$ is R$^{18}$, R$^{19}$, R$^{20}$ or R$^{21}$;

R$^{18}$ is phenyl which is unfused or fused with benzene, heteroarene or R$^{18A}$; R$^{18A}$ is cycloalkane, cycloalkene, heterocycloalkane or heterocycloalkene;

R$^{19}$ is heteroaryl which is unfused or fused with benzene, heteroarene or R$^{19A}$; R$^{19A}$ is cycloalkane, cycloalkene, heterocycloalkane or heterocycloalkene;

R$^{20}$ is C$_3$C$_{10}$-cycloalkyl or C$_4$-C$_{10}$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{20A}$; R$^{20A}$ is cycloalkane, cycloalkene, heterocycloalkane or heterocycloalkene;

R$^{21}$ is alkyl, alkenyl or alkynyl, each of which is unsubstituted or substituted with one or two or three independently selected R$^{22}$, OR$^{22}$, NHR$^{22}$, N(R$^{22}$)$_2$, C(O)NH$_2$, C(O)NHR$^{22}$, C(O)N(R$^{22}$)$_2$, OH, (O), C(O)OH, N$_3$, CN, NH$_2$, CF$_3$, CF$_2$CF$_3$, F, Cl, Br or I substituents;

R$^{22}$ is R$^{23}$, R$^{24}$ or R$^{25}$;

R$^{23}$ is phenyl which is unfused or fused with benzene, heteroarene or R$^{23A}$; R$^{23A}$ is cycloalkane, cycloalkene, heterocycloalkane or heterocycloalkene;

R$^{24}$ is heteroarene which is unfused or fused with benzene, heteroarene or R$^{24}$A; R$^{24A}$ is cycloalkane, cycloalkene, heterocycloalkane or heterocycloalkene;

R$^{25}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{25A}$; R$^{25A}$ is cycloalkane, cycloalkene, heterocycloalkane or heterocycloalkene;

R$^{30}$ is cycloalkyl or cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{30A}$; R$^{30A}$ is cycloalkane, cycloalkene, heterocycloalkane or heterocycloalkene;

wherein R$^{30}$ is substituted with F, Cl, Br, I, CH$_2$R$^{37}$, CH(R$^{31}$)(R$^{37}$), C(R$^{31}$)(R$^{31A}$)(R$^{37}$), C(O)R$^{37}$, OR$^{37}$, SR$^{37}$, S(O)R$^{37}$, SO$_2$R$^{37}$, NHR$^{37}$ or N(R$^{32}$)R$^{37}$;

R$^{31}$ and R$^{31A}$ are independently F, Cl, Br or alkyl or are taken together and are C$_2$-C$_5$-spiroalkyl;

R$^{32}$ is R$^{33}$, C(O)R$^{33}$, or C(O)OR$^{33}$;

R$^{33}$ is R$^{34}$ or R$^{35}$;

R$^{34}$ is phenyl which is unfused or fused with benzene, heteroarene, or R$^{34A}$; R$^{34A}$ is cycloalkane, cycloalkene, heterocycloalkane or heterocycloalkene;

R$^{35}$ is alkyl which is unsubstituted or substituted with R$^{36}$;

R$^{36}$ is phenyl which is unfused or fused with benzene, heteroarene or R$^{36}$A; R$^{36A}$ is cycloalkane, cycloalkene, heterocycloalkane or heterocycloalkene;

R$^{37}$ is R$^{38}$, R$^{39}$ or R$^{40}$, each of which is substituted with F, Cl, Br, I, R$^{41}$, OR$^{41}$, NHR$^{41}$, N(R$^{41}$)$_2$, NHC(O)OR$^{41}$, SR$^{41}$, S(O)R$^{41}$ or SO$_2$R$^{41}$;

R$^{38}$ is phenyl which is unfused or fused with benzene, heteroarene or R$^{38A}$; R$^{38A}$ is cycloalkane, cycloalkene, heterocycloalkane or heterocycloalkene;

R$^{39}$ is heteroaryl which is unfused or fused with benzene, heteroarene or R$^{39A}$; R$^{39A}$ is cycloalkane, cycloalkene, heterocycloalkane or heterocycloalkene;

R$^{40}$ is C$_3$-C$_8$-cycloalkyl or C$_4$-C$_8$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{40A}$; R$^{40A}$ cycloalkane, cycloalkene, heterocycloalkane or heterocycloalkene;

R$^{41}$ is R$^{42}$, R$^{43}$, R$^{44}$ or R$^{45}$;

R$^{42}$ is phenyl which is unfused or fused with benzene, heteroarene or R$^{42A}$; R$^{42A}$ is cycloalkane, cycloalkene, heterocycloalkane or heterocycloalkene;

R$^{43}$ is heteroaryl which is unfused or fused with benzene, heteroarene or R$^{43A}$; R$^{43A}$ is cycloalkane, cycloalkene, heterocycloalkane or heterocycloalkene;

R$^{44}$ is C$_3$-C$_9$-cycloalkyl or C$_4$-C$_7$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{44A}$; R$^{44A}$ is cycloalkane, cycloalkene, heterocycloalkane or heterocycloalkene;

R$^{45}$ is alkyl, alkenyl or alkynyl, each of which is unsubstituted or substituted with one or two independently selected R$^{46}$, OR$^{46}$, NHR$^{46}$, N(R$^{46}$)$_2$, C(O)NH$_2$, C(O)NHR$^{46}$, C(O)N(R$^{46}$)$_2$, OH, (O), C(O)OH, N$_3$, CN, NH$_2$, CF$_3$, CF$_2$CF$_3$, F, Cl, Br or I substituents;

R$^{46}$ is R$^{47}$, R$^{48}$ or R$^{49}$;

R$^{47}$ is phenyl which is unfused or fused with benzene, heteroarene or R$^{47A}$; R$^{47A}$ is cycloalkane, cycloalkene, heterocycloalkane or heterocycloalkene;

R$^{48}$ is heteroaryl or R$^{48A}$; R$^{48A}$ is cycloalkyl, cycloalkenyl, heterocycloalkyl or heterocycloalkenyl;

R$^{49}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{49A}$; R$^{49A}$ is cycloalkane, cycloalkene, heterocycloalkane or heterocycloalkene;

wherein the moieties represented by R$^2$, R$^{2A}$, R$^3$, R$^{3A}$, R$^4$, R$^{4A}$, R$^6$, R$^{6C}$, R$^8$, R$^{8A}$, R$^9$, R$^{9A}$, R$^{10}$, R$^{10A}$, R$^{13}$, R$^{13A}$, R$^{14}$, R$^{14A}$, R$^{15}$, R$^{15A}$, R$^{18}$, R$^{18A}$, R$^{19}$, R$^{19A}$, R$^{20}$, R$^{20A}$, R$^{23}$, R$^{23A}$, R$^{24}$, R$^{24A}$, R$^{25}$, R$^{25A}$, R$^{30}$, R$^{30A}$, R$^{31}$ and R$^{31A}$ taken together, R$^{34}$, R$^{34A}$, R$^{36}$, R$^{36A}$, R$^{38}$, R$^{38A}$, R$^{39}$, R$^{39A}$, R$^{40}$, R$^{40A}$, R$^{42}$, R$^{42A}$, R$^{43}$, R$^{43A}$, R$^{44}$, R$^{44A}$, R$^{47}$, R$^{47A}$, R$^{48}$, R$^{48A}$, R$^{49}$, and R$^{49A}$ are independently unsubstituted, further unsubstituted, substituted or further substituted with one or two or three or four or five independently selected R$^{50}$, OR$^{50}$, SR$^{50}$, S(O)R$^{50}$, SO$_2$R$^{50}$, C(O)R$^{50}$, CO(O)R$^{50}$, OC(O)R$^{50}$, NH$_2$, NHR$^{50}$, N(R$^{50}$)$_2$, C(O)NH$_2$, C(O)NHR$^{50}$, C(O)N(R$^{50}$)$_2$, C(O)NHOH, C(O)NHOR$^{50}$, C(O)NR$^{55}$SO$_2$R$^{50}$, SO$_2$NH$_2$, SO$_2$NHR$^{50}$, SO$_2$N(R$^{50}$)$_2$, CF$_3$, CF$_2$CF$_3$, C(O)H, C(O)OH, C(N)NH$_2$, C(N)NHR$^{50}$, C(N)N(R$^{50}$)$_2$, OH, (O), CN, N$_3$, NO$_2$, CF$_3$, CF$_2$CF$_3$, OCF$_3$, OCF$_2$CF$_3$, F, Cl, Br or I substituents;

R$^{50}$ is R$^{51}$, R$^{52}$, R$^{53}$ or R$^{54}$;

R$^{51}$ is phenyl which is unfused or fused with benzene, heteroarene or R$^{51B}$; R$^{51B}$ is cycloalkane, cycloalkene, heterocycloalkane or heterocycloalkene;

R$^{52}$ is heteroaryl;

R$^{53}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{53B}$;

wherein R$^{53B}$ is cycloalkane, cycloalkene, heterocycloalkane or heterocycloalkene;

R$^{54}$ is alkyl, alkenyl or alkynyl, each of which is unsubstituted or substituted with one or two or three independently selected R$^{55}$, OR$^{55}$, SR$^{55}$, S(O)R$^{55}$, SO$_2$R$^{55}$, NHR$^{55}$, N(R$^{55}$)$_2$, N(R$^{55}$)$_2$, C(O)R$^{55}$, C(O)NH$_2$, C(O)NHR$^{55}$, NHC(O)R$^{55}$, NHSO$_2$R$^{55}$, NHC(O)OR$^{55}$, SO$_2$NH$_2$, SO$_2$NHR$^{55}$, SO$_2$N(R$^{55}$)$_2$, NHC(O)NH$_2$, NHC(O)NHR$^{55}$, OH, (O), C(O) OH, (O), N$_3$, CN, NH$_2$, CF$_3$, OCF$_3$CF$_3$, F, Cl, Br or I substituents;

R$^{55}$ is alkyl, alkenyl, alkynyl, phenyl, heteroaryl or R$^{56}$;

wherein the alkyl, alkenyl, and alkynyl are unsubstituted or substituted with OCH$_3$; and R$^{56}$ is C$_3$-C$_8$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N.

In one embodiment of Formula (I);

A$^1$ is C(A$^2$);
A$^2$ is H;
D$^1$ is H;
E$^1$ is H;
Y$^1$ is NO$_2$;
G$^1$ is R$^{1B}$, OR$^{1B}$, or NHR$^{1B}$;
wherein the R$^{1B}$, or a substituent on R$^{1B}$, is substituted or further substituted with OP(O)(OH)(OH);
R$^1$ and R$^{1B}$ are each independently R$^5$;
R$^5$ is alkyl, which is independently further unsubstituted, or substituted with R$^7$;
R$^7$ is R$^{10}$;
R$^{10}$ is C$_3$-C$_{10}$-cycloalkyl, each having one or two CH$_2$ moieties unreplaced or replaced with independently selected O;
R$^{30}$ is cycloalkyl or cycloalkenyl, each having one or two CH moieties unreplaced or replaced with N;
wherein R$^{30}$ is substituted with CH$_2$R$^{37}$;
R$^{37}$ is R$^{40}$, each of which is substituted with R$^{41}$;
R$^{40}$ is C$_4$-C$_8$-cycloalkenyl;
R$^{41}$ is R$^{42}$;
R$^{42}$ is phenyl;
wherein the moieties represented by R$^{10}$, R$^{40}$, and R$^{42}$ are independently unsubstituted, further unsubstituted, substituted or further substituted with one or two or three or four or five independently selected R$^{50}$, OR$^{50}$, F, Cl, Br or I substituents;
R$^{50}$ is R$^{54}$; and
R$^{54}$ is alkyl.

In another embodiment of Formula (I); A$^1$ is C(A$^2$); and A$^2$ is H. In another embodiment of Formula (I); A$^1$ is C(A$^2$); A$^2$ is H; and D$^1$ is H. In another embodiment of Formula (I); A$^1$ is C(A$^2$); A$^2$ is H; D$^1$ is H; and E$^1$ is H. In another embodiment of Formula (I); A$^1$ is C(A$^2$); A$^2$ is H; D$^1$ is H; E$^1$ is H; and Y$^1$ is NO$_2$.

In one embodiment of Formula (I); G$^1$ is R$^{1B}$, OR$^{1B}$, or NHR$^{1B}$. In another embodiment of Formula (I); A$^1$ is C(A$^2$); A$^2$ is H; D$^1$ is H; E$^1$ is H; Y$^1$ is NO$_2$; and G$^1$ is R$^{1B}$, OR$^{1B}$, or NHR$^{1B}$.

In one embodiment of Formula (I); G$^1$ is R$^{1B}$, OR$^{1B}$, or NHR$^{1B}$; wherein the R$^{1B}$, or a substituent on R$^{1B}$, is substituted or further substituted with OP(O)(OH)(OH). In another embodiment of Formula (I); A$^1$ is C(A$^2$); A$^2$ is H; D$^1$ is H; E$^1$ is H; Y$^1$ is NO$_2$; and G$^1$ is R$^{1B}$, or NHR$^{1B}$; wherein the R$^{1B}$, or a substituent on R$^{1B}$, is substituted or further substituted with OP(O)(OH)(OH).

Still another embodiment pertains to compounds having Formula (I) which are
3-[(4-{[4-(4-{[2-(4-chlorophenyl)-4,4-dimethylcyclohex-1-en-1-yl]methyl}piperzin-1-2-(1H-pyrrolo[2,3-b]pyridin-5-yloxy)benzoyl]sulfamoyl}-2-nitrophenyl)amino]-2,2-dimethylpropyl dihydrogen phosphate;

trans-4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenoxy)methyl]cyclohexyl dihydrogen phosphate; and therapeutically acceptable salts, and metabolites thereof.

One embodiment of this invention, therefore, pertains to compounds or therapeutically acceptable salts, which are useful as selective inhibitors of one or more than one antiapoptotic protein family member, the compounds having Formula (II)

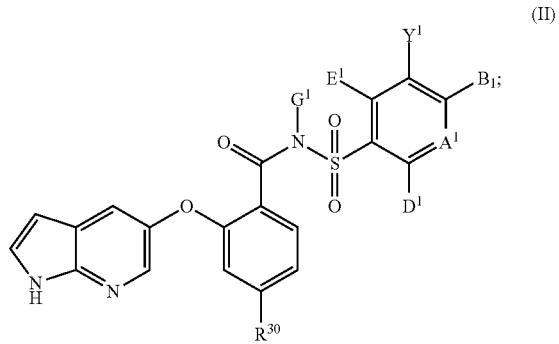

wherein $A^1$ is N or $C(A^2)$;

$A^2$ is H, $R^1$, $OR^1$, $SR^1$, $S(O)R^1$, SO $R^1$ $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2M(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNOR$^1$, $C(O)NHSO_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNOR$^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNON, C(O)NHNOR$^1$, $C(O)NHSO_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$;

$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNOR$^1$, $C(O)NHSO_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$;

$G^1$ is $R^{1B}$, $OR^{1B}$, or $NHR^{1B}$;

wherein the $R^{1B}$, or a substituent on $R^{1B}$, is substituted or further substituted with $S(O)_2(OH)$, $C(O)OR^{50}OP(O)(OH)(OH)$, $C(O)R^{50}OP(O)(OH)(OH)$, $C(O)NH(R^{50})NH_2$, $C(O)R^{50}C(O)NR^{50}$, $OR^{50}P(O)(OH)(OH)$, $OP(O)(OH)(OH)$, or $OC(O)CH_2OP(O)(OH)(OH)$;

$R^1$ and $R^{1B}$ are each independently $R^2$, $R^3$, $R^4$ or $R^5$;

$R^{1A}$ is $C_1$-$C_6$-alkyl, $C_3$-$C_6$-alkenyl or $C_3$-$C_6$-alkynyl;

$R^2$ is phenyl which is unfused or fused with benzene, heteroarene or $R^{2A}$; $R^{2A}$ is cycloalkane or heterocycloalkane;

$R^3$ is heteroaryl which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is independently unsubstituted, further unsubstituted, substituted or further substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl which is unfused or fused with benzene, heteroarene or $R^{8A}$; $R^{8A}$ is cycloalkane, cycloalkene, heterocycloalkane or heterocycloalkene;

$R^9$ is heteroaryl which is unfused or fused with benzene, heteroarene or $R^{9A}$; $R^{9A}$ is cycloalkane, cycloalkene, heterocycloalkane or heterocycloalkene;

$R^{10}$ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $NHR^{12}$, $N(R^{12})_2$, $C(O)NH_2$, $C(O)$ NHR$^{12}$, C(O)N(R$^{12}$)$_2$, OH, (O), C(O)OH, N$_3$, CN, NH$_2$, CF$_3$, CF$_2$CF$_3$, F, Cl, Br or I substituents;

R$^{12}$ is R$^{13}$, R$^{14}$, R$^{15}$ or R$^{16}$;

R$^{13}$ is phenyl which is unfused or fused with benzene, heteroarene or R$^{13A}$; R$^{13A}$ is cycloalkane, cycloalkene, heterocycloalkane or heterocycloalkene;

R$^{14}$ is heteroaryl, each of which is unfused or fused with benzene, heteroarene or R$^{14A}$; R$^{14A}$ is cycloalkane, cycloalkene, heterocycloalkane or heterocycloalkene;

R$^{15}$ is cycloalkane, cycloalkene, heterocycloalkane or heterocycloalkene, each of which is unfused or fused with benzene, heteroarene or R$^{15A}$; R$^{15A}$ is cycloalkane, cycloalkene, heterocycloalkane or heterocycloalkene;

R$^{16}$ is alkyl, alkenyl or alkynyl;

R$^{17}$ is R$^{18}$, R$^{19}$, R$^{20}$ or R$^{21}$;

R$^{18}$ is phenyl which is unfused or fused with benzene, heteroarene or R$^{18A}$; R$^{18A}$ is cycloalkane, cycloalkene, heterocycloalkane or heterocycloalkene;

R$^{19}$ is heteroaryl which is unfused or fused with benzene, heteroarene or R$^{19A}$; R$^{19A}$ is cycloalkane, cycloalkene, heterocycloalkane or heterocycloalkene;

R$^{20}$ is C$_3$-C$_{10}$-cycloalkyl or C$_4$-C$_{10}$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{20A}$; R$^{20A}$ is cycloalkane, cycloalkene, heterocycloalkane or heterocycloalkene;

R$^{21}$ is alkyl, alkenyl or alkynyl, each of which is unsubstituted or substituted with one or two or three independently selected R$^{22}$, OR$^{22}$, NHR$^{22}$, N(R$^{22}$)$_2$, C(O)NH$_2$, C(O)NHR$^{22}$, C(O)N(R$_{22}$)$_2$, OH, (O), C(O)OH, N$_3$, CN, NH$_2$, CF$_3$, CF$_2$CF$_3$, F, Cl, Br or I substituents;

R$^{22}$ is R$^{23}$, R$^{24}$ or R$^{25}$;

R$^{23}$ is phenyl which is unfused or fused with benzene, heteroarene or R$^{23A}$; R$^{23A}$ is cycloalkane, cycloalkene, heterocycloalkane or heterocycloalkene;

R$^{24}$ is heteroarene which is unfused or fused with benzene, heteroarene or R$^{24A}$; R$^{24A}$ is cycloalkane, cycloalkene, heterocycloalkane or heterocycloalkene;

R$^{25}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{25A}$; R$^{25}$A is cycloalkane, cycloalkene, heterocycloalkane or heterocycloalkene;

R$^{30}$ is cycloalkyl or cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{30A}$; R$^{30A}$ is cycloalkane, cycloalkene, heterocycloalkane or heterocycloalkene;

wherein R$^{30}$ is substituted with F, Cl, Br, I, CH$_2$R$^{37}$, CH(R$^{31}$)(R$^{37}$), C(R$^{31}$)(R$^{31A}$)(R$^{37A}$)(R$^{37}$), C(O)R$^{37}$, OR$^{37}$, SR$^{37}$, S(O)R$^{37}$, SO$_2$R$^{37}$, NHR$^{37}$ or N(R$^{32}$)R$^{37}$;

R$^{31}$ and R$^{31A}$ are independently F, Cl, Br or alkyl or are taken together and are C$_2$-C$_5$-spiroalkyl;

R$^{32}$ is R$^{33}$, C(O)R$^{33}$, or C(O)OR$^{33}$;

R$^{33}$ is R$^{34}$ or R$^{35}$;

R$^{34}$ is phenyl which is unfused or fused with benzene, heteroarene, or R$^{34A}$; R$^{34A}$ is cycloalkane, cycloalkene or heterocycloalkane or heterocycloalkene;

R$^{35}$ is alkyl which is unsubstituted or substituted with R$^{36}$;

R$^{36}$ is phenyl which is unfused or fused with benzene, heteroarene or R$^{36A}$; R$^{36A}$ is cycloalkane, cycloalkene, heterocycloalkane or heterocycloalkene;

R$^{37}$ is R$^{38}$, R$^{39}$ or R$^{40}$, each of which is substituted with F, Cl, Br, I, R$^{41}$, OR$^{41}$, NHR$^{41}$, N(R$^{41}$)$_2$, NHC(O)OR$^{41}$, SR$^{41}$, S(O)R$^{41}$ or SO$_2$R$_{41}$;

R$^{38}$ is phenyl which is unfused or fused with benzene, heteroarene or R$^{38A}$; R$^{38A}$ is cycloalkane, cycloalkene, heterocycloalkane or heterocycloalkene;

R$^{39}$ is heteroaryl which is unfused or fused with benzene, heteroarene or R$^{39A}$; R$^{39A}$ is cycloalkane, cycloalkene, heterocycloalkane or heterocycloalkene;

R$^{40}$ is C$_3$-C$_8$-cycloalkyl or C$_4$-C$_8$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{40A}$; R$^{40A}$ cycloalkane, cycloalkene, heterocycloalkane or heterocycloalkene;

R$^{41}$ is R$^{42}$, R$^{43}$, R$^{44}$ or R$^{45}$;

R$^{42}$ is phenyl which is unfused or fused with benzene, heteroarene or R$^{42A}$; R$^{42A}$ is cycloalkane, cycloalkene, heterocycloalkane or heterocycloalkene;

R$^{43}$ is heteroaryl which is unfused or fused with benzene, heteroarene or R$^{43A}$; R$^{43A}$ is cycloalkane, cycloalkene, heterocycloalkane or heterocycloalkene;

R$^{44}$ is C$_3$-C$_9$-cycloalkyl or C$_4$-C$_7$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{44A}$; R$^{44A}$ is cycloalkane, cycloalkene, heterocycloalkane or heterocycloalkene;

R$^{45}$ is alkyl, alkenyl or alkynyl, each of which is unsubstituted or substituted with one or two independently selected R$^{46}$, OR$^{46}$, NHR$^{46}$, N(R$^{46}$)$_2$, C(O)NH$_2$, C(O)NHR$^{46}$, C(O)N(R$^{46}$)$_2$, OH, (O), C(O)OH, N$_3$, CN, NH$_2$, CF$_3$, CF$_2$CF$_3$, F, Cl, Br or I substituents;

R$^{46}$ is R$^{47}$, R$^{48}$ or R$^{49}$;

R$^{47}$ is phenyl which is unfused or fused with benzene, heteroarene or R$^{47A}$; R$^{47A}$ is cycloalkane, cycloalkene, heterocycloalkane or heterocycloalkene;

R$^{48}$ is heteroaryl or R$^{48A}$; R$^{48A}$ is cycloalkyl, cycloalkenyl, heterocycloalkyl or heterocycloalkenyl;

R$^{49}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{49A}$; R$^{49A}$ is cycloalkane, cycloalkene, heterocycloalkane or heterocycloalkene;

wherein the moieties represented by R$^2$, R$^{2A}$, R$^3$, R$^{3A}$, R$^4$, R$^{4A}$, R$^6$, R$^{6C}$, R$^8$, R$^{8A}$, R$^9$, R$^{9A}$, R$^{10}$, R$^{10A}$, R$^{13}$, R$^{13A}$, R$^{14}$, R$^{14A}$, R$^{15}$, R$^{15A}$, R$^{18}$, R$^{18A}$, R$^{19}$, R$^{19A}$, R$^{20}$, R$^{20A}$, R$^{23}$, R$^{23A}$, R$^{24}$, R$^{24A}$m R$^{25}$, R$^{25A}$, R$^{30}$, R$^{30A}$, R$^{31}$ and R$^{31A}$ taken together, R$^{34}$, R$^{34A}$, R$^{36}$, R$^{36A}$, R$^{38}$, R$^{38A}$, R$^{39}$, R$^{39A}$, R$^{40}$, R$^{40A}$, R$^{42}$, R$^{42A}$, R$^{43}$, R$^{43A}$, R$^{44}$, R$^{44A}$, R$^{47}$, R$^{47A}$, R$^{48}$, R$^{48A}$, R$^{49}$, and R$^{49A}$ are independently unsubstituted, further unsubstituted, substituted or further substituted with one or two or three or four or five independently selected R$^{50}$, OR$^{50}$, SR$^{50}$, S(O)R$^{50}$, SO$_2$R$^{50}$, C(O)R$^{50}$, CO(O)R$^{50}$, OC(O)R$^{50}$, OC(O)OR$^{50}$, NH$_2$, NHR$^{50}$, N(R$^{50}$)$_2$, C(O)NH$_2$, C(O)NHR$^{50}$, C(O)N(R$^{50}$)$_2$, C(O)NHOH, C(O)NHOR$^{50}$, C(O)NHSO$_2$R$^{50}$, C(O)NR$^{55}$SO$_2$R$^{50}$, SO$_2$NH$_2$, SO$_2$NHR$^{50}$, SO$_2$N(R$^{50}$)$_2$, CF$_3$, CF$_2$CF$_3$, C(O)H, C(O)OH, C(N)NH$_2$, C(N)

NHR$^{50}$, C(N)N(R$^{50}$)$_2$, OH, (O), CN, N$_3$, NO$_2$, CF$_3$, CF$_2$CF$_3$, OCF$_3$, OCF$_2$CF$_3$, F, Cl, Br or I substituents;

R$^{50}$ is R$^{51}$, R$^{52}$, R$^{53}$ or R$^{54}$;

R$^{51}$ is phenyl which is unfused or fused with benzene, heteroarene or R$^{51B}$; R$^{51B}$ is cycloalkane, cycloalkene, heterocycloalkane or heterocycloalkene;

R$^{52}$ is heteroaryl;

R$^{53}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{53B}$;

wherein R$^{53B}$ is cycloalkane, cycloalkene, heterocycloalkane or heterocycloalkene;

R$^{54}$ is alkyl, alkenyl or alkynyl, each of which is unsubstituted or substituted with one or two or three independently selected R$^{55}$, OR$^{55}$, SR$^{55}$, S(O)R$^{55}$, SO$_2$R$^{55}$, NHR$^{55}$, N(R$^{55}$)$_2$, C(O)R$^{55}$, C(O)NH$_2$, C(O)NHR$^{55}$, NHC(O)R$^{55}$, NHSO$_2$R$^{55}$, NHC(O)OR$^{55}$, SO$_2$NH$_2$, SO$_2$NHR$^{55}$, SO$_2$N(R$^{55}$)$_2$, NHC(O)NH$_2$, NHC(O)NHR$^{55}$, OH, (O), C(O)OH, (O), N$_3$, CN, NH$_2$, CF$_3$, OCF$_3$, CF$_2$CF$_3$, OCF$_2$CF$_3$, F, Cl, Br or I substituents;

R$^{55}$ is alkyl, alkenyl, alkynyl, phenyl, heteroaryl or R$^{56}$;

wherein the alkyl, alkenyl, and alkynyl are unsubstituted or substituted with OCH$_3$; and R$^{56}$ is C$_3$-C$_8$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N.

In one embodiment of Formula (II);
A$^1$ is C(A$^2$);
A$^2$ is H;
B$^1$ is OR$^1$, or NHR$^1$;
D$^1$ is H;
E$^1$ is H;
Y$^1$ is NO$_2$;
G$^1$ is R$^{1B}$, OR$^{1B}$, or NHR$^{1B}$;
wherein the R$^{1B}$, or a substituent on R$^{1B}$, is substituted or further substituted with OP(O)(OH)(OH);
R$^1$ and R$^{1B}$ are each independently R$^5$;
R$^5$ is alkyl, which is independently further unsubstituted, or substituted with R$^7$;
R$^7$ is R$^{10}$;
R$^{10}$ is C$_3$-C$_{10}$-cycloalkyl, each having one or two CH$_2$ moieties unreplaced or replaced with independently selected O;
R$^{30}$ is cycloalkyl or cycloalkenyl, each having one or two CH moieties unreplaced or replaced with N;
wherein R$^{30}$ is substituted with CH$_2$R$^{37}$;
R$^{37}$ is R$^{40}$, each of which is substituted with R$^{41}$;
R$^{40}$ is C$_4$-C$_8$-cycloalkenyl;
R$^{41}$ is R$^{42}$;
R$^{42}$ is phenyl;
wherein the moieties represented by R$^{10}$, R$^{40}$, and R$^{42}$ are independently unsubstituted, further unsubstituted, substituted or further substituted with one or two or three or four or five independently selected R$^{50}$, OR$^{50}$, F, Cl, Br or I substituents;
R$^{50}$ is R$^{54}$; and
R$^{54}$ is alkyl.

In another embodiment of Formula (II); A$^1$ is C(A$^2$); and A$^2$ is H. In another embodiment of Formula (II); A$^1$ is C(A$^2$); A$^2$ is H; and B$^1$ is OR$^1$, or NHR$^1$. In another embodiment of Formula (II); A$^1$ is C(A$^2$); A$^2$ is H; B$^1$ is OR$^1$, or NHR$^1$; and D$^1$ is H. In another embodiment of Formula (II); A$^1$ is C(A$^2$); A$^2$ is H; B$^1$ is OR$^1$, or NHR$^1$; D$^1$ is H; and E$^1$ is H. In another embodiment of Formula (II); A$^1$ is C(A$^2$); A$^2$ is H; B$^1$ is OR$^1$, or NHR$^1$; D$^1$ is H; E$^1$ is H; and Y$^1$ is NO$_2$.

In one embodiment of Formula (II); G$^1$ is R$^{1B}$, OR$^{1B}$, or NHR$^{1B}$. In another embodiment of Formula (II); A$^1$ is C(A$^2$); A$^2$ is H; B$^1$ is OR$^1$, or NHR$^1$; D$^1$ is H; E$^1$ is H; Y$^1$ is NO$_2$; and G$^1$ is R$^{1B}$, OR$^{1B}$, or NHR$^{1B}$.

In one embodiment of Formula (II); G$^1$ is R$^{1B}$, OR$^{1B}$, or NHR$^{1B}$; wherein the R$^{1B}$, or a substituent on R$^{1B}$, is substituted or further substituted with OP(O)(OH)(OH). In another embodiment of Formula (II); A$^1$ is C(A$^2$); A$^2$ is H; B$^1$ is OR$^1$ or NHR$^1$; D$^1$ is H; E$^1$ is H; Y$^1$ is NO$_2$; and G$^1$ is R$^{1B}$, OR$^{1B}$, or NHR$^{1B}$; wherein the R$^{1B}$, or a substituent on R$^{1B}$, is substituted or further substituted with OP(O)(OH)(OH).

One embodiment of this invention, therefore, pertains to compounds or therapeutically acceptable salts, which are useful as selective inhibitors of one or more than one anti-apoptotic protein family member, the compounds having Formula (III)

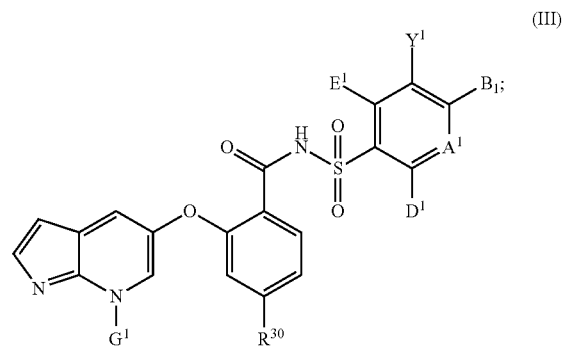

wherein
A$^1$ is N or C(A$^2$);
A$^2$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{14}$;

B$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{14}$;

D$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$,

NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{14}$;

E$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{14}$; and Y$^1$ is H, CN, NO$_2$, C(O)OH, F, Cl, Br, I, CF$_3$, OCF$_3$, CF$_2$CF$_3$, OCF$_2$CF$_3$, R$^{17}$, OR$^{17}$, C(O)R$^{17}$, C(O)OR$^{17}$, SR$^{17}$, NH$_2$, NHR$^{17}$, N(R$^{17}$)$_2$, NHC(O)R$^{17}$, C(O)NH$_2$, C(O)NHR$^{17}$, C(O)N(R$^{17}$)$_2$, NHS(O)R$^{17}$ or NHSO$_2$R$^{17}$;

G$^1$ is R$^{1B}$, OR$^{1B}$, or NHR$^{1B}$;

wherein the R$^{1B}$, or a substituent on R$^{1B}$, is substituted or further substituted with S(O)$_2$(OH), C(O)OR$^{50}$OP(O)(OH)(OH), C(O)R$^{50}$OP(O)(OH)(OH), C(O)NH(R$^{50}$)NH$_2$, C(O)R$^{50}$C(O)NR$^{50}$; OR$^{50}$P(O)(OH)(OH), OP(O)(OH)(OH), or OC(O)CH$_2$OP(O)(OH)(OH);

R$^1$ and R$^{1B}$ are each independently R$^2$, R$^3$, R$^4$ or R$^5$;

R$^{14}$ is C$_1$-C$_6$-alkyl, C$_3$-C$_6$-alkenyl or C$_3$-C$_6$-alkynyl;

R$^2$ is phenyl which is unfused or fused with benzene, heteroarene or R$^{2A}$; R$^{2A}$ is cycloalkane or heterocycloalkane;

R$^3$ is heteroaryl which is unfused or fused with benzene, heteroarene or R$^{3A}$; R$^{3A}$ is cycloalkane or heterocycloalkane;

R$^4$ is cycloalkyl, cycloalkenyl, heterocycloalkyl or heterocycloalkenyl, each of which is unfused or fused with benzene, heteroarene or R$^{4A}$; R$^{4A}$ is cycloalkane, cycloalkene, heterocycloalkane or heterocycloalkene;

R$^5$ is alkyl, alkenyl or alkynyl, each of which is independently unsubstituted, further unsubstituted, substituted or further substituted with one or two or three independently selected R$^6$, NC(R$^{6A}$)(R$^{6B}$), R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, NHC(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, NHC(O)CH(CH$_3$)NHC(O)CH(CH$_3$)NHR$^1$, OH, (O), C(O)OH, (O), N$_3$, CN, NH$_2$, CF$_3$, CF$_2$CF$_3$, F, Cl, Br or I substituents;

R$^6$ is C$_2$-0$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^7$ is R$^8$, R$^9$, R$^{10}$ or R$^{11}$;

R$^8$ is phenyl which is unfused or fused with benzene, heteroarene or R$^{8A}$; R$^{8A}$ is cycloalkane, cycloalkene, heterocycloalkane or heterocycloalkene;

R$^9$ is heteroaryl which is unfused or fused with benzene, heteroarene or R$^{9A}$; R$^{9A}$ is cycloalkane, cycloalkene, heterocycloalkane or heterocycloalkene;

R$^{10}$ is C$_3$-C$_{10}$-cycloalkyl or C$_4$-C$_{10}$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{10A}$; R$^{10A}$ is cycloalkane, cycloalkene, heterocycloalkane or heterocycloalkene;

R$^{11}$ is alkyl, alkenyl or alkynyl, each of which is unsubstituted or substituted with one or two or three independently selected R$^{12}$, OR$^{12}$, NHR$^{12}$, N(R$^{12}$)$_2$, C(O)NH$_2$, C(O)NHR$^{12}$, C(O)N(R$^{12}$)$_2$, OH, (O), C(O)OH, N$_3$, CN, NH$_2$, CF$_3$, CF$_2$CF$_3$, F, Cl, Br or I substituents;

R$^{12}$ is R$^{13}$, R$^{14}$, R$^{15}$ or R$^{16}$;

R$^{13}$ is phenyl which is unfused or fused with benzene, heteroarene or R$^{13A}$; R$^{13A}$ is cycloalkane, cycloalkene, heterocycloalkane or heterocycloalkene;

R$^{14}$ is heteroaryl, each of which is unfused or fused with benzene, heteroarene or R$^{14A}$; R$^{14A}$ is cycloalkane, cycloalkene, heterocycloalkane or heterocycloalkene;

R$^{15}$ is cycloalkane, cycloalkene, heterocycloalkane or heterocycloalkene, each of which is unfused or fused with benzene, heteroarene or R$^{15A}$; R$^{15A}$ is cycloalkane, cycloalkene, heterocycloalkane or heterocycloalkene;

R$^{16}$ is alkyl, alkenyl or alkynyl;

R$^{17}$ is R$^{18}$, R$^{19}$, R$^{20}$ or R$^{21}$;

R$^{18}$ is phenyl which is unfused or fused with benzene, heteroarene or R$^{18A}$; R$^{18A}$ is cycloalkane, cycloalkene, heterocycloalkane or heterocycloalkene;

R$^{19}$ is heteroaryl which is unfused or fused with benzene, heteroarene or R$^{19A}$; R$^{19A}$ is cycloalkane, cycloalkene, heterocycloalkane or heterocycloalkene;

R$^{20}$ is C$_3$-C$_{10}$-cycloalkyl or C$_4$-C$_{10}$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{20A}$; R$^{20A}$ is cycloalkane, cycloalkene, heterocycloalkane or heterocycloalkene;

R$^{21}$ is alkyl, alkenyl or alkynyl, each of which is unsubstituted or substituted with one or two or three independently selected R$^{22}$, OR$^{22}$, NHR$^{22}$, N(R$^{22}$)$_2$, C(O)NH$_2$, C(O)NHR$^{22}$, C(O)M(R$^{22}$)$_2$, OH, (O), C(O)OH, N$_3$, CN, NH$_2$, CF$_3$, CF$_2$CF$_3$, F, Cl, Br or I substituents;

R$^{22}$ is R$^{23}$, R$^{24}$ or R$^{25}$;

R$^{23}$ is phenyl which is unfused or fused with benzene, heteroarene or R$^{23A}$; R$^{23A}$ is cycloalkane, cycloalkene, heterocycloalkane or heterocycloalkene;

R$^{24}$ is heteroarene which is unfused or fused with benzene, heteroarene or R$^{24A}$; R$^{24A}$ is cycloalkane, cycloalkene, heterocycloalkane or heterocycloalkene;

R$^{25}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{25A}$; R$^{25A}$ is cycloalkane, cycloalkene, heterocycloalkane or heterocycloalkene;

R$^{30}$ is cycloalkyl or cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or R$^{30A}$; R$^{30A}$ is cycloalkane, cycloalkene, heterocycloalkane or heterocycloalkene;

wherein R$^{30}$ is substituted with F, Cl, Br, I, CH$_2$R$^{37}$, CH(R$^{31}$)(R$^{37}$), C(R$^{31}$)(R$^{31A}$)(R$^{37}$), C(O)R$^{37}$, OR$^{37}$, SR$^{37}$, S(O)R$^{37}$, SO$_2$R$^{37}$, NHR$^{37}$ or N(R$^{32}$)R$^{37}$;

R$^{31}$ and R$^{31A}$ are independently F, Cl, Br or alkyl or are taken together and are C$_2$-C$_5$-spiroalkyl;

$R^{32}$ is $R^{33}$, C(O)$R^{33}$, or C(O)O$R^{33}$;

$R^{33}$ is $R^{34}$ or $R^{35}$;

$R^{34}$ is phenyl which is unfused or fused with benzene, heteroarene, or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, O$R^{41}$, NH$R^{41}$, N($R^{41}$)$_2$, NHC(O)O$R^{41}$, S$R^{41}$, S(O)$R^{41}$ or SO$_2$$R^{41}$;

$R^{38}$ is phenyl which is unfused or fused with benzene, heteroarene or $R^{38A}$; $R^{38A}$ is cycloalkane, cycloalkene, heterocycloalkane or heterocycloalkene;

$R^{39}$ is heteroaryl which is unfused or fused with benzene, heteroarene or $R^{39A}$; $R^{39A}$ is cycloalkane, cycloalkene, heterocycloalkane or heterocycloalkene;

$R^{40}$ is $C_3$-$C_8$-cycloalkyl or $C_4$-$C_8$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with benzene, heteroarene or $R^{42A}$; $R^{42A}$ is cycloalkane, cycloalkene, heterocycloalkane or heterocycloalkene;

$R^{43}$ is heteroaryl which is unfused or fused with benzene, heteroarene or $R^{43A}$; $R^{43A}$ is cycloalkane, cycloalkene, heterocycloalkane or heterocycloalkene;

$R^{44}$ is $C_3$-$C_9$-cycloalkyl or $C_4$-$C_7$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, O$R^{46}$, NH$R^{46}$, N($R^{46}$)$_2$, C(O)NH$_2$, C(O)NH$R^{46}$, C(O)N($R^{46}$)$_2$, OH, O, C(O)OH, N$_3$, CN, NH$_2$, CF$_3$, CF$_2$CF$_3$, F, Cl, Br or I substituents;

$R^{46}$ is $R^{47}$, $R^{48}$ or $R^{49}$;

$R^{47}$ is phenyl which is unfused or fused with benzene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkyl, cycloalkenyl, heterocycloalkyl or heterocycloalkenyl;

$R^{49}$ is $C_3$-$C_6$-cycloalkyl or $C_4$-$C_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{49A}$; $R^{49A}$ is cycloalkane, cycloalkene, heterocycloalkane or heterocycloalkene;

wherein the moieties represented by $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{18}$, $R^{18A}$, $R^{19}$, $R^{19A}$, $R^{20}$, $R^{20A}$, $R^{23}$, $R^{23A}$, $R^{24}$, $R^{24A}$, $R^{25}$, $R^{25A}$, $R^{30}$, $R^{30A}$, $R^{31}$ and $R^{31A}$ taken together, $R^{34}$, $R^{34A}$, $R^{36}$, $R^{36A}$, $R^{38}$, $R^{38A}$, $R^{39}$, $R^{39A}$, $R^{40}$, $R^{40A}$, $R^{42}$, $R^{42A}$, $R^{43}$, $R^{43A}$, $R^{44}$, $R^{44A}$, $R^{47}$, $R^{47A}$, $R^{48}$, $R^{48A}$, $R^{49}$, and $R^{49A}$ are independently unsubstituted, further unsubstituted, substituted or further substituted with one or two or three or four or five independently selected $R^{50}$, O$R^{50}$, S$R^{50}$, S(O)$R^{50}$, SO$_2$$R^{50}$, C(O)$R^{50}$, CO(O)$R^{50}$, OC(O)O$R^{50}$, NH$_2$, NH$R^{50}$, N($R^{50}$)$_2$, C(O)NH$_2$, C(O)NH$R^{50}$, C(O)N($R^{50}$)$_2$, C(O)NHOH, C(O)NHO$R^{50}$, C(O)NHSO$_2$$R^{50}$, C(O)N$R^{55}$SO$_2$$R^{50}$, SO$_2$NH$_2$, SO$_2$NH$R^{50}$, SO$_2$N($R^{50}$)$_2$, CF$_3$, CF$_2$CF$_3$, C(O)H, C(O)OH, C(N)NH$_2$, C(N)NH$R^{50}$, C(N)N($R^{50}$)$_2$, OH, (O), CN, N$_3$, NO$_2$, CF$_3$, CF$_2$CF$_3$, OCF$_3$, OCF$_2$CF$_3$, F, Cl, Br or I substituents;

$R^{50}$ is $R^{51}$, $R^{52}$, $R^{53}$ or $R^{54}$;

$R^{51}$ is phenyl which is unfused or fused with benzene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, O$R^{55}$, S$R^{55}$, S(O)$R^{55}$, SO$_2$$R^{55}$, NH$R^{55}$, N($R^{55}$)$_2$, C(O)$R^{55}$, C(O)NH$_2$, C(O)NH$R^{55}$, NHC(O)$R^{55}$, NHSO$_2$$R^{55}$, NHC(O)O$R^{55}$, SO$_2$NH$_2$, SO$_{NHR}^{55}$, SO$_2$N($R^{55}$)$_2$, NHC(O)NH$_2$, NHC(O)NH$R^{55}$, OH, (O), C(O)OH, (O), N$_3$, CN, NH$_2$, CF$_3$, OCF$_3$, CF$_2$CF$_3$, OCF$_2$CF$_3$, F, Cl, Br or I substituents;

$R^{55}$ is alkyl, alkenyl, alkynyl, phenyl, heteroaryl or $R^{56}$;

wherein the alkyl, alkenyl, and alkynyl are unsubstituted or substituted with OCH$_3$; and $R^{56}$ is $C_3$-$C_8$-cycloalkyl or $C_4$-$C_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N.

In one embodiment of Formula (III);

$A^1$ is C($A^2$);

$A^2$ is H;

$B^1$ is O$R^1$, or NH$R^1$;

$D^1$ is H;

$E^1$ is H;

$Y^1$ is NO$_2$;

$G^1$ is $R^{1B}$, O$R^{1B}$, or NH$R^{1B}$;

wherein the $R^{1B}$, or a substituent on $R^{1B}$, is substituted or further substituted with OP(O)(OH)(OH);

$R^1$ and $R^{1B}$ are each independently $R^5$;

$R^5$ is alkyl, which is independently further unsubstituted, or substituted with $R^7$;

$R^7$ is $R^{10}$;

$R^{10}$ is $C_3$-$C_{10}$-cycloalkyl, each having one or two CH$_2$ moieties unreplaced or replaced with independently selected O;

$R^{30}$ is cycloalkyl or cycloalkenyl, each having one or two CH moieties unreplaced or replaced with N;

wherein $R^{30}$ is substituted with CH$_2$$R^{37}$;

$R^{37}$ is $R^{40}$, each of which is substituted with $R^{41}$;

$R^{40}$ is $C_4$-$C_8$-cycloalkenyl;

$R^{41}$ is $R^{42}$;

$R^{42}$ is phenyl;

wherein the moieties represented by $R^{10}$, $R^{40}$, and $R^{42}$ are independently unsubstituted, further unsubstituted, substituted or further substituted with one or two or three or four or five independently selected $R^{50}$, O$R^{50}$, F, Cl, Br or I substituents;

$R^{50}$ is $R^{54}$; and $R^{54}$ is alkyl.

In another embodiment of Formula (III); $A^1$ is C($A^2$); and $A^2$ is H. In another embodiment of Formula (III); $A^1$ is C($A^2$); $A^2$ is H; and $B^1$ is O$R^1$, or NH$R^1$. In another embodiment of Formula (III); $A^1$ is C($A^2$); $A^2$ is H; $B^1$ is O$R^1$, or NH$R^1$; and $D^1$ is H. In another embodiment of Formula (III); $A^1$ is C($A^2$); $A^2$ is H; $B^1$ is O$R^1$, or NH$R^1$; $D^1$ is H; and $E^1$ is H. In another embodiment of Formula (III); $A^1$ is C($A^2$); $A^2$ is H; $B^1$ is O$R^1$, or NH$R^1$; $D^1$ is H; $E^1$ is H; and $Y^1$ is NO$_2$.

In one embodiment of Formula (III); $G^1$ is $R^{1B}$, $DR^{1B}$, or $NHR^{1B}$. In another embodiment of Formula (III); $A^1$ is $C(A^2)$; $A^2$ is H; $B^1$ is $OR^1$, or $NHR^1$; $D^1$ is H; $E^1$ is H; $Y^1$ is $NO_2$; and $G^1$ is $R^{1B}$, $OR^{1B}$, or $NHR^{1B}$.

In one embodiment of Formula (III); $G^1$ is $R^{1B}$, $OR^{1B}$, or $NHR^{1B}$; wherein the $R^{1B}$, or a substituent on $R^{1B}$, is substituted or further substituted with OP(O)(OH)(OH). In another embodiment of Formula (III); $A^1$ is $C(A^2)$; $A^2$ is H; $B^1$ is $OR^1$ or $NHR^1$; $D^1$ is H; $E^1$ is H; $Y^1$ is $NO_2$; and $G^1$ is $R^{1B}$, $OR^{1B}$, or $NHR^{1B}$; wherein the $R^{1B}$, or a substituent on $R^{1B}$, is substituted or further substituted with OP(O)(OH)(OH).

Still another embodiment pertains to compounds having Formula (III) which are (5-{5-(4-{[2-(4-chlorophenyl)-4,4-dimethylcyclohex-1-en-1-yl]methyl}piperazin-1-yl)-2-[({3-nitro-4-[(tetrahydro-2H-pyran-4-ylmethyl)amino]phenyl}sulfonyl)carbamoyl]phenoxy}-7H-pyrrolo[2,3-b]pyridin-7-yl)methyl dihydrogen phosphate;

{5-[5-(4-{[2-(4-chlorophenyl)-4,4-dimethylcyclohex-1-en-1-yl]methyl}piperazin-1-yl)-2-{[(4-{[(trans-4-methoxycyclohexyl)methyl]amino}-3-nitrophenyl)sulfonyl]carbamoyl}phenoxy]-7H-pyrrolo[2,3-b]pyridin-7-yl}methyl dihydrogen phosphate;

(5-{5-(4-{[2-(4-chlorophenyl)-4,4-dimethylcyclohex-1-en-1-yl]methyl}piperazin-1-yl)-2-[({4-[(4-fluorotetrahydro-2H-pyran-4-yl)methoxy]-3-nitrophenyl}sulfonyl)carbamoyl]phenoxy}-7H-pyrrolo[2,3-b]pyridin-7-yl)methyl dihydrogen phosphate; and therapeutically acceptable salts, and metabolites thereof.

One embodiment of this invention, therefore, pertains to compounds or therapeutically acceptable salts, which are useful as selective inhibitors of one or more than one anti-apoptotic protein family member, the compounds having Formula (Ia), (IIa), or (IIIa)

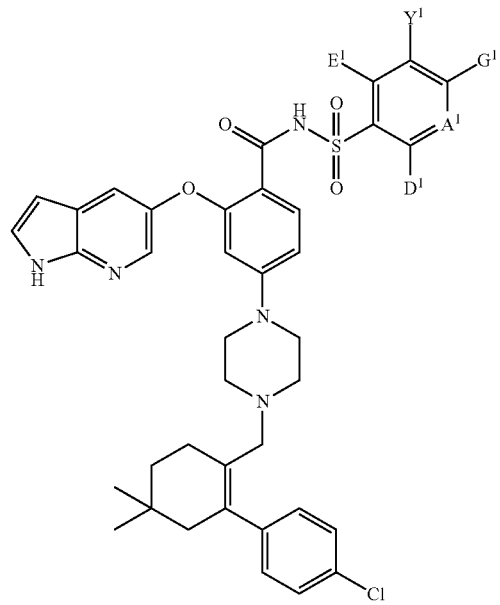

(Ia)

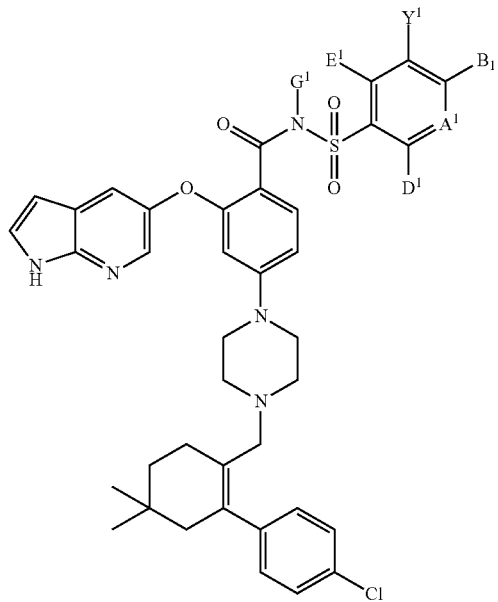

(IIa)

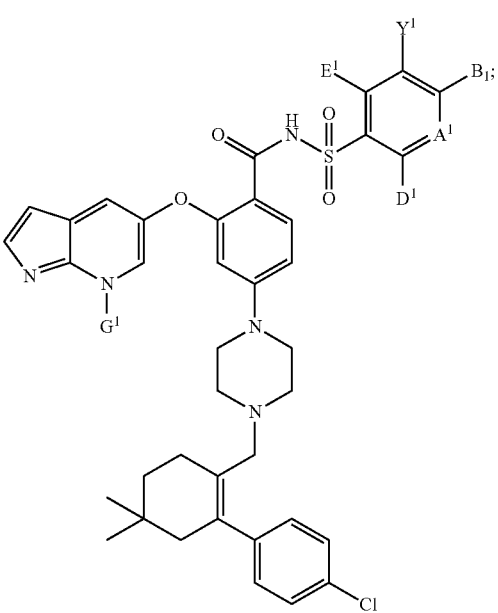

(IIIa)

wherein $A^1$ is N or $C(A^2)$;

$A^2$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNOR$^1$, C(O)NHSO$_2$R$^1$, C(NH)NH$_2$, C(NH)NHR$^1$, C(NH)N(R$^1$)$_2$, NHSO$_2$NHR$^1$, NHSO$_2$N(CH$_3$)R$^1$, N(CH$_3$)SO$_2$N(CH$_3$)R$^1$, F, Cl, Br, I, CN, $NO_2$, $N_3$, OH, C(O)H, CHNOH, CH(NOCH$_3$), CF$_3$, C(O)OH, C(O)NH$_2$ or C(O)OR$^{1A}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)R$^1$, NR$^1$C(O)R$^1$, NHC(O)OR$^1$, NR$^1$C(O)OR$^1$, NHC(O)

NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂ NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR¹ᴬ;

D¹ is H, R¹, OR¹, SR¹, S(O)R¹, SO₂R¹, C(O)R¹, C(O)OR¹, OC(O)R¹, NHR³, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂ NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR¹ᴬ;

E¹ is H, R¹, OR¹, SR¹, S(O)R¹, SO₂R¹, C(O)R¹, C(O)OR¹, OC(O)R¹, NHR¹, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR¹ᴬ; and Y¹ is H, CN, NO₂, C(O)OH, F, Cl, Br, I, CF₃, OCF₃, CF₂CF₃, OCF₂CF₃, R¹⁷, OR¹⁷, C(O)R¹⁷, C(O)OR¹⁷, SR¹⁷, NH₂, NHR¹⁷, N(R¹⁷)₂, NHC(O)R¹⁷, C(O)NH₂, C(O)NHR¹⁷, C(O)N(R¹⁷)₂, NHS(O)R¹⁷ or NHSO₂R¹⁷;

G¹ is R¹ᴮ, OR¹ᴮ, or NHR¹ᴮ;

wherein the R¹ᴮ, or a substituent on R¹ᴮ, is substituted or further substituted with S(O)₂(OH), C(O)OR⁵⁰OP(O)(OH)(OH), C(O)R⁵⁰OP(O)(OH)(OH), C(O)NH(R⁵⁰)NH₂, C(O)R⁵⁰C(O)NR⁵⁰; OR⁵⁰P(O)(OH)(OH), OP(O)(OH)(OH), or OC(O)CH₂P(O)(OH)(OH);

R¹ and R¹ᴮ are each independently R², R³, R⁴ or R⁵;

R¹ᴬ is C₁-C₆-alkyl, C₃-C₆-alkenyl or C₃-C₆-alkynyl;

R² is phenyl which is unfused or fused with benzene, heteroarene or R²ᴬ; R²ᴬ is cycloalkane or heterocycloalkane;

R³ is heteroaryl which is unfused or fused with benzene, heteroarene or R³ᴬ; R³ᴬ is cycloalkane or heterocycloalkane;

R⁴ is cycloalkyl, cycloalkenyl, heterocycloalkyl or heterocycloalkenyl, each of which is unfused or fused with benzene, heteroarene or R⁴ᴬ; R⁴ᴬ is cycloalkane, cycloalkene, heterocycloalkane or heterocycloalkene;

R⁵ is alkyl, alkenyl or alkynyl, each of which is independently unsubstituted, further unsubstituted, substituted or further substituted with one or two or three independently selected R⁶, NC(R⁶ᴬ)(R⁶ᴮ), R⁷, OR⁷, SR⁷, S(O)R⁷, SO₂R⁷, NHR⁷, N(R⁷)₂, C(O)R⁷, C(O)NH₂, C(O)NHR⁷, NHC(O)R⁷, NHSO₂R⁷, NHC(O)OR⁷, SO₂NH₂, SO₂NHR⁷, SO₂N(R⁷)₂, NHC(O)NH₂, NHC(O)NHR⁷, NHC(O)CH(CH₃)NHC(O)CH(CH₃)NH₂, NHC(O)CH(CH₃)NHC(O)CH(CH₃)NHR¹, OH, (O), C(O)OH, (O), N₃, CN, NH₂, CF₃, CF₂CF₃, F, Cl, Br or I substituents;

R⁶ is C₂-C₅-spiroalkyl, each of which is unsubstituted or substituted with OH, (O), N₃, CN, CF₃, CF₂CF₃, F, Cl, Br, I, NH₂, NH(CH₃) or N(CH₃)₂;

R⁶ᴬ and R⁶ᴮ are independently selected alkyl or, together with the N to which they are attached, R⁶ᶜ;

R⁶ᶜ is aziridin-1-yl, azetidin-1-yl, pyrrolidin-1-yl or piperidin-1-yl, each having one CH₂ moiety unreplaced or replaced with O, C(O), CNOH, CNOCH₃, S, S(O), SO₂ or NH;

R⁷ is R⁸, R⁹, R¹⁰ or R¹¹;

R⁸ is phenyl which is unfused or fused with benzene, heteroarene or R⁸ᴬ; R⁸ᴬ is cycloalkane, cycloalkene, heterocycloalkane or heterocycloalkene;

R⁹ is heteroaryl which is unfused or fused with benzene, heteroarene or R⁹ᴬ; R⁹ᴬ is cycloalkane, cycloalkene, heterocycloalkane or heterocycloalkene;

R¹⁰ is C₃-C₁₀-cycloalkyl or C₄-C₁₀-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with benzene, heteroarene or R¹⁰ᴬ; R¹⁰ᴬ is cycloalkane, cycloalkene, heterocycloalkane or heterocycloalkene;

R¹¹ is alkyl, alkenyl or alkynyl, each of which is unsubstituted or substituted with one or two or three independently selected R¹², OR¹², NHR¹², N(R¹²)₂, C(O)NH₂, C(O)NHR¹², C(O)N(R¹²)₂, OH, (O), C(O)OH, N₃, CN, NH₂, CF₃, CF₂CF₃, F, Cl, Br or I substituents;

R¹² is R¹³, R¹⁴, R¹⁵ or R¹⁶;

R¹³ is phenyl which is unfused or fused with benzene, heteroarene or R¹³ᴬ; R¹³ᴬ is cycloalkane, cycloalkene, heterocycloalkane or heterocycloalkene;

R¹⁴ is heteroaryl, each of which is unfused or fused with benzene, heteroarene or R¹⁴ᴬ; R¹⁴ᴬ is cycloalkane, cycloalkene, heterocycloalkane or heterocycloalkene;

R¹⁵ is cycloalkane, cycloalkene, heterocycloalkane or heterocycloalkene, each of which is unfused or fused with benzene, heteroarene or R¹⁵ᴬ; R¹⁵ᴬ is cycloalkane, cycloalkene, heterocycloalkane or heterocycloalkene;

R¹⁶ is alkyl; alkenyl or alkynyl;

R¹⁷ is R¹⁸, R¹⁹, R²⁰ or R²¹;

R¹⁸ is phenyl which is unfused or fused with benzene, heteroarene or R¹⁸ᴬ; R¹⁸ᴬ is cycloalkane, cycloalkene, heterocycloalkane or heterocycloalkene;

R¹⁹ is heteroaryl which is unfused or fused with benzene, heteroarene or R¹⁹ᴬ; R¹⁹ᴬ is cycloalkane, cycloalkene, heterocycloalkane or heterocycloalkene;

R²⁰ is C₃-C₁₀-cycloalkyl or C₄-C₁₀-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with benzene, heteroarene or R²⁰ᴬ; R²⁰ᴬ is cycloalkane, cycloalkene, heterocycloalkane or heterocycloalkene;

R²¹ is alkyl, alkenyl or alkynyl, each of which is unsubstituted or substituted with one or two or three independently selected R²², OR²², NHR²², N(R²²)₂, C(O)NH₂, C(O)NHR²², C(O)N(R²²)₂, OH, (O), C(O)OH, N₃, CN, NH₂, CF₃, CF₂CF₃, F, Cl, Br or I substituents;

R²² is R²³, R²⁴ or R²⁵;

R²³ is phenyl which is unfused or fused with benzene, heteroarene or R²³ᴬ; R²³ᴬ is cycloalkane, cycloalkene, heterocycloalkane or heterocycloalkene;

R²⁴ is heteroarene which is unfused or fused with benzene, heteroarene or R²⁴ᴬ; R²⁴ᴬ is cycloalkane, cycloalkene, heterocycloalkane or heterocycloalkene;

R²⁵ is C₃-C₆-cycloalkyl or C₄-C₆-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with benzene, heteroarene or $R^{25A}$; $R^{25A}$ is cycloalkane, cycloalkene, heterocycloalkane or heterocycloalkene;

wherein moieties represented by $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{18}$, $R^{18A}$, $R^{19}$, $R^{19A}$, $R^{20}$, $R^{20A}$, $R^{23}$, $R^{23A}$, $R^{24}$, $R^{24A}$, $R^{25}$, $R^{25A}$, are independently unsubstituted, further unsubstituted, substituted or further substituted with one or two or three or four or five independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{55}SO_2R^{50}$, $SO_2NH_2$, $SO_2NHR^{50}$, $SO_2N(R^{50})_2$, $CF_3$, $CF_2CF_3$, $C(O)H$, $C(O)OH$, $C(N)NH_2$, $C(N)NHR^{50}$, $C(N)N(R^{50})_2$, $OH$, $(O)$, $CN$, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl which is unfused or fused with benzene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $NHR^{55}$, $N(R^{55})_2$, $C(O)R^{55}$, $C(O)NH_2$, $C(O)NHR^{55}$, $NHC(O)R^{55}$, $NHSO_2R^{55}$, $NHC(O)OR^{55}$, $SO_2NH_2$, $SO_2NHR^{55}$, $SO_2N(R^{55})_2$, $NHC(O)NH_2$, $NHC(O)NHR^{55}$, OH, (O), C(O)OH, (O), $N_3$, CN, $NH_2$, $CF_3$, $OCF_3$, $CF_2CF_3$, $OCF_2CF_3$, F, Cl, Br or I substituents;

$R^{55}$ is alkyl, alkenyl, alkynyl, phenyl, heteroaryl or $R^{56}$;

wherein the alkyl, alkenyl, and alkynyl are unsubstituted or substituted with OCH$_3$; and $R^{56}$ is $C_3$-$C_8$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N.

In one embodiment of Formula (Ia), (IIa), or (IIIa);
$A^1$ is $C(A^2)$;
$A^2$ is H;
$B^1$ is $OR^1$, or $NHR^1$;
$D^1$ is H;
$E^1$ is H;
$Y^1$ is $NO_2$;
$G^1$ is $R^{1B}$, $OR^{1B}$, or $NHR^{1B}$;
wherein the $R^{1B}$, or a substituent on $R^{1B}$, is substituted or further substituted with OP(O)(OH)(OH);
$R^1$ and $R^{1B}$ are each independently $R^5$;
$R^5$ is alkyl, which is independently further unsubstituted, or substituted with $R^7$;
$R^7$ is $R^{10}$;
$R^{10}$ is $C_3$-$C_{10}$-cycloalkyl, each having one or two $CH_2$ moieties unreplaced or replaced with independently selected O;
wherein the moieties represented by $R^{10}$ are independently unsubstituted, further unsubstituted, substituted or further substituted with one or two or three or four or five independently selected $R^{50}$, $OR^{50}$, F, Cl, Br or I substituents;

$R^{50}$ is $R^{54}$; and
$R^{54}$ is alkyl.

In another embodiment of Formula (Ia), (IIa), or (IIIa); $A^1$ is $C(A^2)$; and $A^2$ is H. In another embodiment of Formula (Ia), (IIa), or (IIIa); $A^1$ is $C(A^2)$; $A^2$ is H; and $B^1$ is $OR^1$, or $NHR^1$. In another embodiment of Formula (Ia), (IIa), or (IIIa); $A^1$ is $C(A^2)$; $A^2$ is H; $B^1$ is $OR^1$, or $NHR^1$; and $D^1$ is H. In another embodiment of Formula (Ia), (IIa), or (IIIa); $A^1$ is $C(A^2)$; $A^2$ is H; $B^1$ is $OR^1$, or $NHR^1$; $D^1$ is H; and $E^1$ is H. In another embodiment of Formula (Ia), (IIa), or (IIIa); $A^1$ is $C(A^2)$; $A^2$ is H; $B^1$ is $OR^1$, or $NHR^1$; $D^1$ is H; $E^1$ is H; and $Y^1$ is $NO_2$.

In one embodiment of Formula (Ia), (IIa), or (IIIa); $G^1$ is $R^{1B}$, $OR^{1B}$, or $NHR^{1B}$. In another embodiment of Formula (Ia), (IIa), or (IIIa); $A^1$ is $C(A^2)$; $A^2$ is H; $B^1$ is $OR^1$, or $NHR^1$; $D^1$ is H; $E^1$ is H; $Y^1$ is $NO_2$; and $G^1$ is $R^{1B}$, $OR^{1B}$, or $NHR^{1B}$.

In one embodiment of Formula (Ia), (IIa), or (IIIa); $G^1$ is $R^{1B}$, $OR^{1B}$, or $NHR^{1B}$; wherein the $R^{1B}$, or a substituent on $R^{1B}$, is substituted or further substituted with OP(O)(OH)(OH). In another embodiment of Formula (Ia), (IIa), or (IIIa); $A^1$ is $C(A^2)$; $A^2$ is H; $B^1$ is $OR^1$ or $NHR^1$; $D^1$ is H; $E^1$ is H; $Y^1$ is $NO_2$; and $G^1$ is $R^{1B}$, $OR^{1B}$, or $NHR^{1B}$; wherein the $R^{1B}$, or a substituent on $R^{1B}$, is substituted or further substituted with OP(O)(OH)(OH).

Still another embodiment pertains to compounds having Formula (Ia), (IIa) or (IIIa) which are (5-{5-(4-{[2-(4-chlorophenyl)-4,4-dimethylcyclohex-1-en-1-yl]methyl}piperazin-1-yl)-2-[({3-nitro-4-[(tetrahydro-2H-pyran-4-ylmethyl)amino]phenyl}sulfonyl)carbamoyl]phenoxy}-7H-pyrrolo[2,3-b]pyridin-7-yl)methyl dihydrogen phosphate;

{5-[5-(4-{[2-(4-chlorophenyl)-4,4-dimethylcyclohex-1-en-1-yl]methyl}piperazin-1-yl)-2-{[(4-{[(trans-4-methoxycyclohexyl)methyl]amino}-3-nitrophenyl)sulfonyl]carbamoyl}phenoxy]-7H-pyrrolo[2,3-b]pyridin-7-yl}methyl dihydrogen phosphate;

(5-{5-(4-{[2-(4-chlorophenyl)-4,4-dimethylcyclohex-1-en-1-yl]methyl}piperazin-1-yl)-2-[({4-[(4-fluorotetrahydro-2H-pyran-4-yl)methoxy]-3-nitrophenyl}sulfonyl)carbamoyl]phenoxy}-7H-pyrrolo[2,3-b]pyridin-7-yl)methyl dihydrogen phosphate;

3-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]-2,2-dimethylpropyl dihydrogen phosphate;

trans-4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenoxy)methyl]cyclohexyl dihydrogen phosphate; and therapeutically acceptable salts, and metabolites thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-2 proteins are expressed, said compositions comprising an excipient and a therapeutically effective amount of the compound having Formula (I).

Still another embodiment pertains to methods of treating disease in a patient during which anti-apoptotic Bcl-2 proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-2 proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-2 proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with anti-apoptotic Bcl-2 proteins.

Certain precursor compounds which may be metabolized in vitro or in vivo to form compounds having Formula (I) may also have utility for treating diseases associated with expression of anti-apoptotic Bcl-2 proteins.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiqutin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9)

inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-(trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II, GA101, ofatumumab, ABT-806 (mAb-806), ErbB3 specific antibodies, BSG2 specific antibodies, DLL4 specific antibodies and C-met specific antibodies, and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE® ,(IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of anti-apoptotic Bcl-2 proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp (tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure For Solid-Phase Peptide Synthesis (SPPS)

Peptides were synthesized with, at most, 250 μmol preloaded Wang resin/vessel on an ABI 433A peptide synthesizer using 250 μmol scale Fastmoc™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) From Lysine

The resin from the synthesizer was washed thrice with dichloromethane and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of N,N-dimethylformamide was flowed through the bed over 15 minutes. The resin was then washed thrice with N,N-dimethylformamide and filtered. Ninhydrin tests showed a strong signal for primary amine.

Resin Labeling With 6-Carboxyfluorescein-NHS (6-FAM-NHS)

The resin was treated with 2 equivalents 6-FAM-NHS in 1% DIEA/N,N-dimethylformamide and stirred or shaken at ambient temperature overnight. When complete, the resin was drained, washed thrice with N,N-dimethylformamide, thrice with (1× DCM and 1× methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 μm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D CHEMSTATION software version A.03.04 (Hewlett-Packard. Palo Alto, Calif.) on a 4.6×250 mm YMC column packed with ODS-AQ 5 μm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak: Peptide Probe
Acetyl-GQVGRQLAIIGDK(6-FAM)INR-NH, (SEQ ID NO:1)

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 [(M+H)$^+$].

Alternative Synthesis of Peptide Probe F-Bak:
Acetyl-GQVGRQLAIIGDK(6-FAM)INR-NH, (SEQ ID NO:1)

The protected peptide was assembeled on 0.25 mmol Fmoc-Rink amide MBHA resin (Novabiochem) on an Applied Biosystems 433A automated peptide synthesizer running FASTMOC™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide.

Single-isomer 6 carboxyfluorescein-NHS was reacted with the lysine side-chain in 1% DIEA in N,N-dimethylformamide and confirmed complete by ninhydrin testing. The peptide was cleaved from the resin and side-chains deprotected by treating with 80:5:5:5:2.5:2.5 TFA/water/phenol/thioanisole/triisopropylsilane: 3,6-dioxa-1,8-octanedithiol (v/v/v/v/v v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z =2137.1 ((M+H)+)).

Time Resolved-Fluorescence Resonance Energy Transfer (TR-FRET) Assay

Representative compounds were serially diluted in dimethyl su foxide (DMSO) starting at 50 μM (2×starting concentration; 10% DMSO) and 10 μL were transferred into a 384-well plate. Then 10 μL of a protein/probe/antibody mix was added to each well at final concentrations listed in TABLE 1. The samples are then mixed on a shaker for 1 minute and incubated for an additional 3 hours at room temperature. For each assay, the probe/antibody and protein/probe/antibody were included on each assay plate as negative and positive controls, respectively. Fluorescence was measured on the ENVISION plate reader (Perkin Elmer) using a 340/35 nm excitation filter and 520/525 (F-Bak peptide) and 495/510 nm (Tb-labeled anti-Histidine antibody) emission filters. Inhibition constants (Ki) are shown in TABLE 2 below and were determined using Wang's equation (Wang Z.-X. An Exact Mathematical Expression For Describing Competitive Binding Of Two Different Ligands To A Protein Molecule. *FEBS Lett*. 1995, 360:111-4).

TABLE 1

Protein, Probe And Antibody Used For TR-FRET Assays

| Protein | Probe | Protein (nM) | Probe (nM) | Antibody | Antibody (nM) |
|---|---|---|---|---|---|
| GST-Bcl-2 | F-Bak Peptide Probe Acetyl-GQVGRQLAIIGDK (6-FAM) INR-amide (SEQ ID NO: 1) | 1 | 100 | Tb-anti-GST | 1 |

6-FAM = 6-carboxyfluorescein.; Tb = terbium; GST = glutathione S-transferase

Inhibition constants ($K_i$) for compounds according to the invention are shown in TABLE 2 below. Where the $K_i$ for a compound is represented as ">" (greater than) a certain numerical value, it is intended to mean that the binding affinity value is greater than the limits of detection of the assay used. Where the $K_i$ for a compound is represented as "<" (less than) a certain numerical value, it is intended to mean that the binding affinity value is lower than the limit of detection of the assay used.

TABLE 2

TR-FRET Bcl-2 Binding Ki (μM)

| Example No. | TR-FRET Binding: Bcl-2 Ki (μM) |
|---|---|
| 1 | <0.000010 |
| 2 | <0.000010 |
| 3 | <0.000010 |
| 4 | <0.000010 |
| 5 | <0.000010 |

The inhibition constant ($K_i$) is the dissociation constant of an enzyme-inhibitor complex or a protein/small molecule complex, wherein the small molecule is inhibiting binding of one protein to another protein. So a large $K_i$ value indicates a low binding affinity and a small $K_i$ value indicates a high binding affinity.

The data in TABLE 2 shows inhibition constants for the inhibition of a Bak BH3 peptide probe to Bcl-2 protein and indicate that compounds according to the invention have high binding affinities for anti-apoptotic Bcl-2 protein. The compounds are therefore expected to have utility in treatment of diseases during which anti-apoptotic Bcl-2 protein is expressed.

RS4;11 Cell Viability Assay

The acute lymphoblastic leukemia (ALL) cell line RS4;11 was used as the primary human cell line to assess the cellular activity of Bcl-2 selective agents in vitro and their efficacy in vivo. Previous studies have shown by BH3 profiling, a mitochondrial assay that classifies blocks in the intrinsic apoptotic pathway, that RS4;11 cells were highly dependant on BCL-2 for survival and sensitive to the Bcl-2 family member inhibitor ABT-737 (Blood, 2008, Vol. 111, 2300-2309). The prevalence of Bcl-2 complexed to the proapoptotic BH3 protein Bim in RS4;11 suggests that these cells are "primed" or more susceptible to cell death by antagonism of the antiapoptotic protein Bcl-2 for which they depend on for survival.

RS4;11 cells were cultured in RPMI-1640 supplemented with 2 mM L-glutamine, 10% FBS, 1 mM sodium pyruvate, 2 mM HEPES, 1% penicillin/streptomycin (Invitrogen), 4.5 g/L glucose and maintained at 37 C containing 5% $CO_2$. To test for the cellular activity of compounds in vitro, cells were treated at 50,000 cells per well in 96-well microtiter plates in the presence of 10% human serum for 48 hours in a humidified chamber with 5% $CO_2$. Cell cytotoxicity $EC_{50}$ values were assessed using CellTiter Glo (Promega) according to the manufacturer's recommendations. The $EC_{50}$ values were determined as a percentage of viable cells following treatment compared to the untreated control cells.

TABLE 3

RS4; 11 $EC_{50}$ Values (μM)

| EXAMPLE # | $EC_{50}$ |
|---|---|
| 1 | 0.31 |
| 2 | 0.18 |
| 3 | 0.041 |
| 4 | >1 |
| 5 | 0.042 |

TABLE 3 shows the utility of compounds having Formula I to functionally inhibit anti-apoptotic Bcl-2 protein in a cellular context. The acute lymphoblastic leukemia (ALL) cell line RS4;11 has been shown by BH3 profiling, a mitochondrial assay that classifies blocks in the intrinsic apoptotic pathway, to be highly dependant on Bcl-2 for survival and is sensitive to the Bcl-2 family member inhibitor ABT-737 (*Blood*, 2008, Vol. 111, 2300-2309). The ability of compounds to kill RS4;11 cells is a direct measure of the compounds ability to inhibit anti-apoptotic Bcl-2 protein function. Compounds of Formula I are very effective in killing RS4;11 cells as demonstrated by low $EC_{50}$ values.

The neutral form of compounds are generally and considerably more permeable than the charged form (Chakrabarti, A. C.; Clark-Lewis, I.; Harrigan, P. R.; Cullis, P. R. *Biophysical Journal*. 1992, 61, 228-234). Furthermore, the presence of a charged residue can result in a permeability rate of up to $10^{10}$ times slower than that observed for the corresponding neutral species (Ellens, H.; Eddy, E. P.; Lee, C.; Dougherty, P.; Lago, A.; Xiang, J.; Elliot, J. D.; Cheng, H.; Ohlstein, E.; Smith, P. *Advanced Drug Delivery Reviews*. 1997, 23, 99-109). Compounds of this invention contain a phosphate group, which is expected to be negatively charged at physiological pH, in addition to an acylsufonamide moiety, which is also expected to be negatively charged at physiological pH. It is therefore expected that compounds of the invention, which contain multiple negative charges at physiological pH, would not be able to penetrate the cell membrane of RS4;11 cells and induce apoptosis, or programmed cell death. As demonstrated in Table 3, compounds of this invention are unexpectedly capable of penetrating the cell membrane and inducing programmed cell death.

Solubility Determination

Reagents used included 0.1N HCl, J T Baker Lot G08515; and 50 mM Phosphate pH 7.4, μ=0.155 w/NaCl, NB93214-089. Equipment/Instruments used included balance: Mettler Toledo, UMX2, LC805269; Rainin Pipette: 1000 μL RF09683 μL, 200 μL RF20783; water bath: Vankel, L C 954896, set at 25° C. and 25 RPM, Thermometer: TB085699); and water bath: Vankel, L C 127535, set at 37° C. and 25 RPM, Thermometer: TB096544).

Examples were tested in aqueous media at 25° C. or 37° C. Excess amount of the bulk drug was weighed out and mixed with an aliquot of target media in a clear glass vial. The vial was sealed with cap and wrapped with aluminum foil, then tumbled in a 25° C. or 37° C. water bath as appropriate. When equilibration was completed, the samples were removed from the water bath and the final pH's were measured. The suspensions were filtered through 4 mm, 0.2 μm Millex-LG syringe filters (hydrophilic PTFE membrane, Millipore, Lot N9JN70696). Each filter was used only for one sample and the first three droplets were discarded. The filtrate was assayed after appropriate dilution with the same solvent as used for stock solution. Three replicates were prepared. The concentration of the sample was calculated against the calibration curve for the compound.

TABLE 4

Aqueous Solubility at pH 7.4

| Example | Aqueous Solubility (pH 7.4, ug/mL |
|---|---|
| 1 | >1159 |
| 2 | >4820 |
| 3 | >10850 |
| 4 | 169 |
| 5 | >6580 |
| 1M | <1 |
| 2B | <4 |
| 3E | <1 |
| 6 | <1 |
| 7 | <1 | nd = not determined

The data in Table 4 shows the increased aqueous solubility of Examples 1-5, which are compounds of this invention, over the parent compounds Examples 1M, 2B, 3E, 6, and 7.

The importance of solubility on immediate-release solid oral dosage forms can be found at U.S. Department of Health and Human Services, Food and Drug Administration. Waiver of In Vivo Bioavailability and Bioequivalence Studies for Immediate-Release Solid Oral Dosage Forms Based on a Biopharmaceutics Classification System. Food and Drug Administration Center for Drug Evaluation and Research (CDER) [online], August 2000[retrieved May 19, 2010]. Retrieved from the Internet:<URL: http://www.fda.gov/downloads/Drugs/GuidanceComplianceRegulatory-Information/Guidances/ucm07 0246.pdf>.

A report on the influence of solubility on the oral bioavailability of drugs can be found at WEI-QUIN TONG. Developability Assessment Supporting Drug Candidate Selection. Integrated Drug Product Development Process, University of Utah [online], Jul. 17-19, 2006 [retrieved May 14, 2010]. Retrieved from the Internet:<URL: http://www.pharmacy.utah.edu/pharmaceutics/pdf/Developability.pdf>.

It is expected that, because compounds having Formula I bind to Bcl-2, they would also have utility as binders to anti-apoptotic proteins having close structural homology to Bcl-2, such as, for example, anti-apoptotic Bcl-$X_L$, Bcl-w, Mcl-1 and Bfl-1/A1 proteins.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, chronic lymphocytic leukemia, myeloma, prostate cancer spleen cancer, and the like is described in commonly-owned PCT US 2004/36770, published as WO 2005/049593, and PCT US 2004/37911, published as WO 2005/024636. Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351 (14), 1409-1418.

Involvement of Bcl-2 proteins in arthritis is disclosed in commonly-owned U.S. Provisional Patent Application Ser. No. 60/988,479.

Involvement of Bcl-2 proteins in bone marrow transplant rejection is disclosed in commonly-owned U.S. patent application Ser. No. 11/941,196.

Overexpression of Bcl-2 proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds having Formula (I) would inhibit growth of cells expressing Bcl-2 proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B *streptococci* (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, mycobacterium avium intracellulare, mycobacterium tuberculosis, myelodysplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthopathy, sporadic, polyglandular deficiency type I, sporadic polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

SCHEME 1

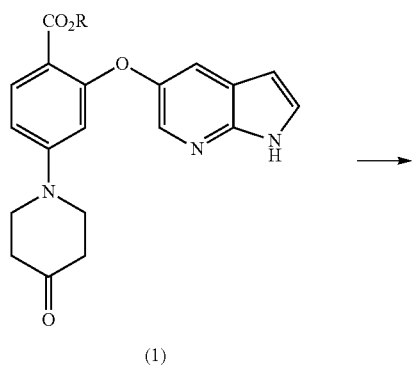

(1)

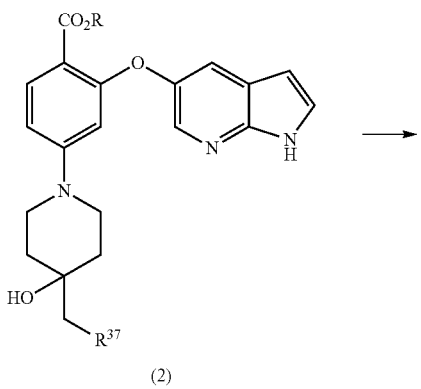

(2)

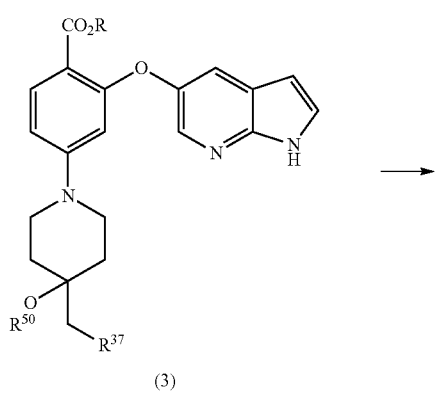

(3)

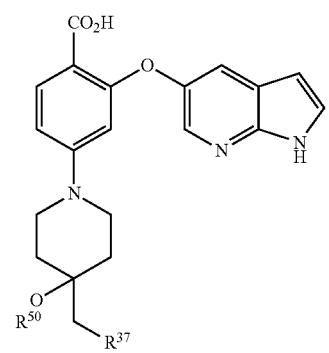

(4)

Compounds of Formula (4) can be prepared as shown in SCHEME 1, and can be used as described in SCHEME 7 to prepare compounds of Formula (I), which are representative of the compounds of the present invention. Compounds of Formula (I) wherein R is alkyl, can be converted to compounds of Formula (2) using $R^{37}CH_2MgX^1$, wherein $X^1$ is a halide, in a solvent such as but not limited to ether or tetrahydrofuran. Compounds of Formula (3) can be prepared from compounds of Formula (2) using a strong base such as NaH and $R^{50}X^2$, wherein $X^2$ is a halide and $R^{50}$ is as described herein. Compounds of Formula (3), when treated with aqueous NaOH or LiOH, will provide compounds of Formula (4).

SCHEME 2

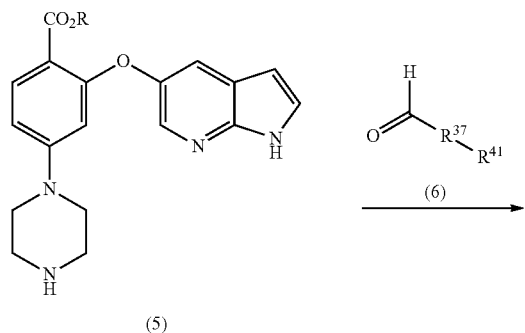

SCHEME 3

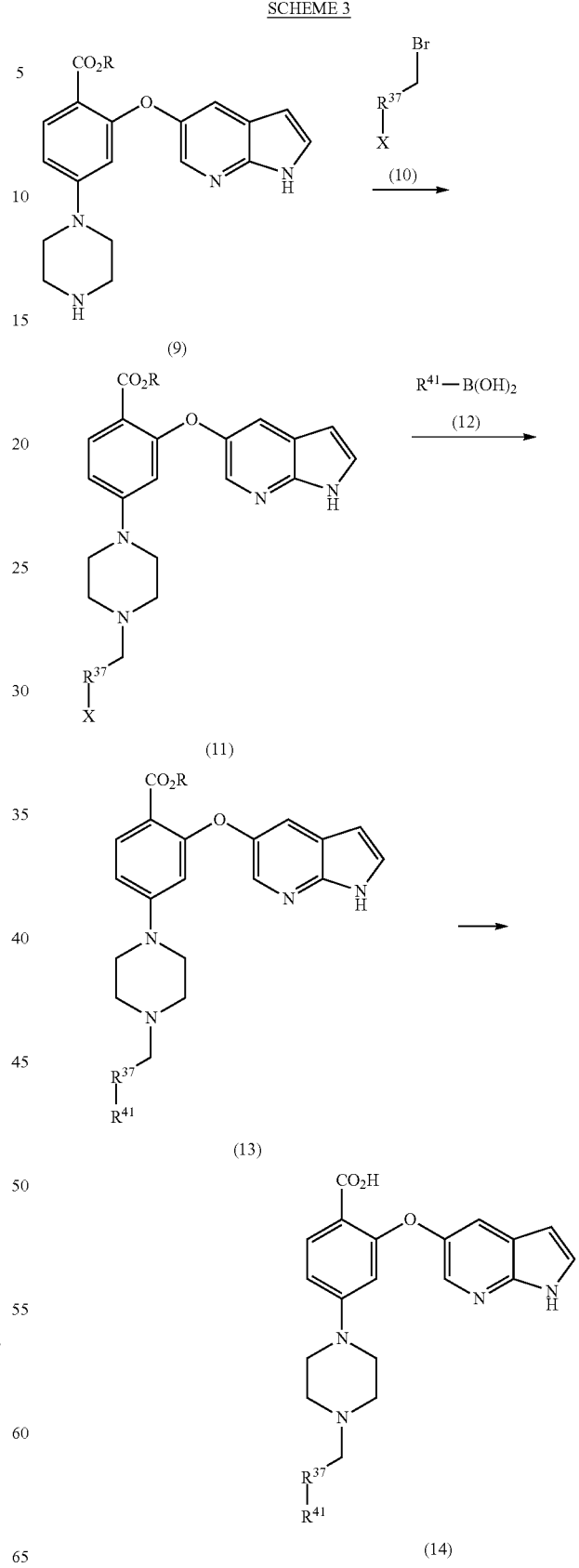

As shown in SCHEME 2, compounds of Formula (5) can be reacted with compounds of Formula (6) and a reducing agent to provide compounds of Formula (7). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, and dichloromethane or mixtures thereof. Compounds of Formula (8) can be prepared from compounds of Formula (7) as described in SCHEME 1, and can be used as described in SCHEME 7 to prepare compounds of Formula (I).

Compounds of Formula (9), when reacted with a compound a Formula (10) wherein X is a halide or triflate, and a base will provide a compound of Formula (11). Bases useful in the reaction include triethylamine, diisopropylethylamine and the like. Compounds of Formula (13), wherein $R^{41}$ is as described herein for substituents on $R^{37}$, can be prepared from compounds of Formula (11) and compounds of Formula (12) using Suzuki coupling conditions known to those skilled in the art and readily available in the literature. Compounds of Formula (14) can be prepared from compounds of Formula (13) as described in SCHEME 1, and can be used as described in SCHEME 7 to prepare compounds of Formula (I).

-continued

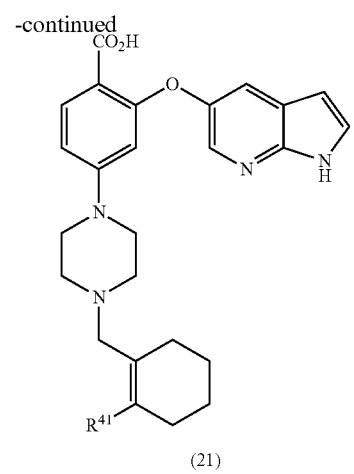

(21)

As shown in SCHEME 4, compounds of Formula (17) can be prepared from compounds of Formula (15) and compounds of Formula (16), wherein R is alkyl and $R^{41}$ is as described herein, using Suzuki coupling conditions known to those skilled in the art and readily available in the literature. Compounds of Formula (17) can be reduced to compounds of Formula (18) using a reducing agent such as $LiAlH_4$ in a solvent such as but not limited to diethyl ether or THF. Compounds of Formula (19) can be prepared from compounds of Formula (18) using Dess-Martin periodinane or Swern oxidation conditions known to those skilled in the art and readily available in the literature. Compounds of Formula (19) can be reacted with a compound of Formula (5) and a reducing agent to provide compounds of Formula (20). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, 1,2-dichloroethane, and dichloromethane or mixtures thereof Compounds of Formula (21) can be prepared from compounds of Formula (20) as described in SCHEME 1, and can be used as described in SCHEME 7 to prepare compounds of Formula (I).

SCHEME 4

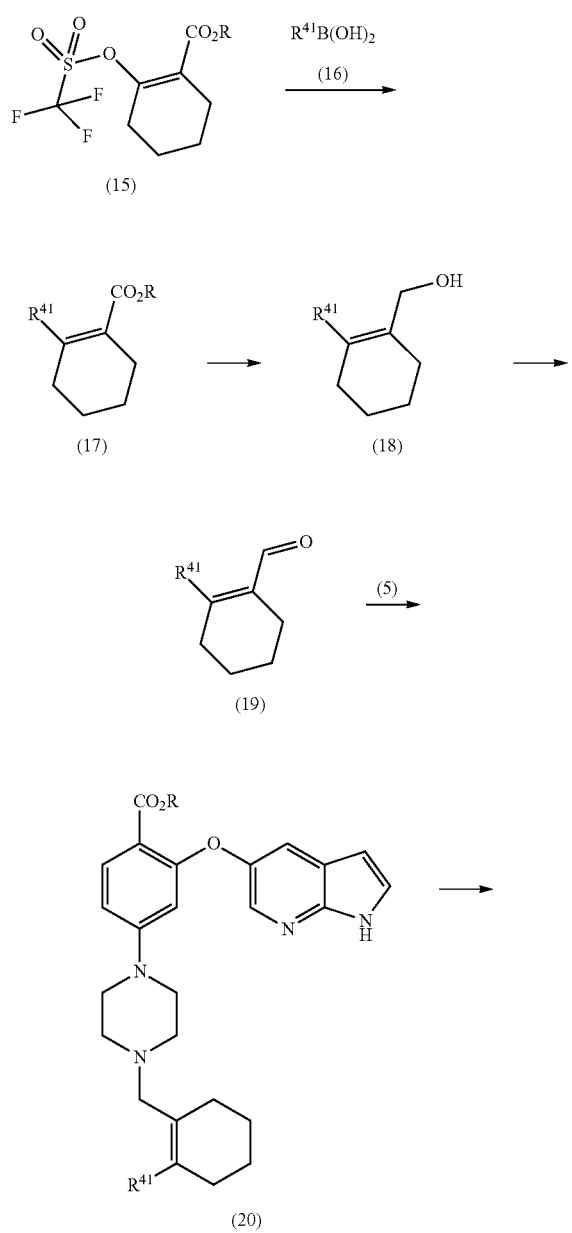

SCHEME 5

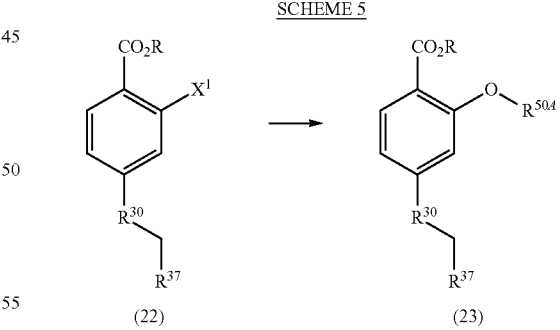

As shown in SCHEME 5, compounds of Formula (22), wherein R is alkyl, may be converted to compounds of Formula (23) by reacting the former, wherein $X^1$ is Cl, Br, I, or $CF_3SO_3$—, and compounds of Formula $R^{50A}$—OH, wherein $R^{50A}$ is 1H-pyrrolo[2,3-b]pyridinyl, and a catalyst, with or without a first base. Examples of catalysts include copper(I) trifluoromethanesulfonate toluene complex, $PdCl_2$, $Pd(OAc)_2$, and $Pd_2(dba)_3$. Examples of first bases include triethylamine, N,N-diisopropylethylamine, $Cs_2CO_3$, $Na_2CO_3$, $K_3PO_4$, and mixtures thereof.

Compounds of Formula (22) may also be converted to compounds of Formula (23) by reacting the former, when $X^1$ is Cl, F, or $NO_2$, and compounds of Formula $R^{50A}$—OH with a first base. Examples of first bases include triethylamine, N,N-diisopropylethylamine, $Cs_2CO_3$, $Na_2CO_3$, $K_3PO_4$, and mixtures thereof.

SCHEME 6

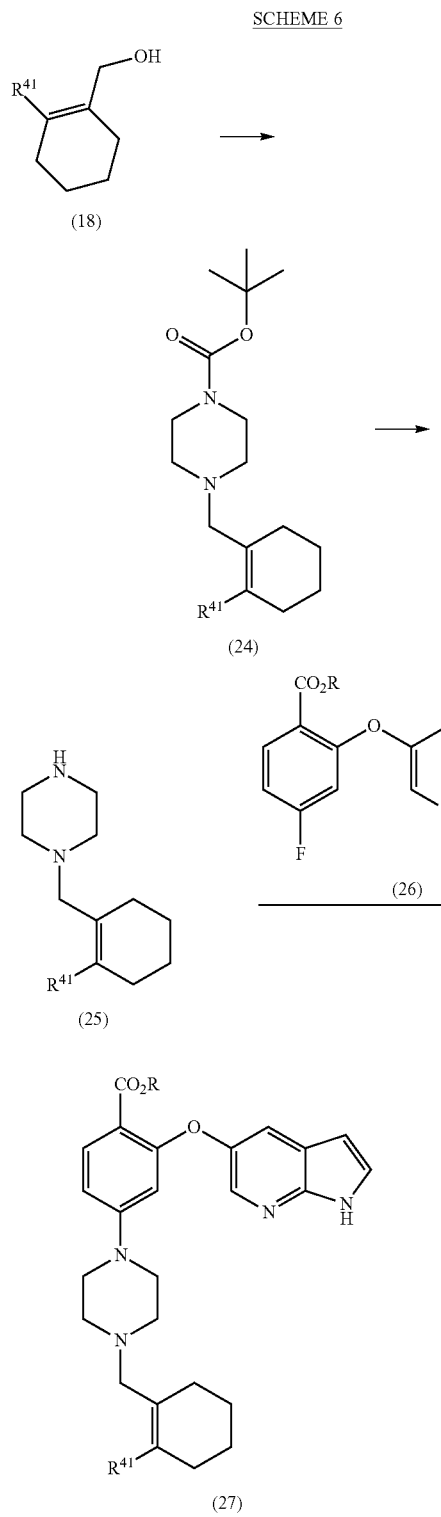

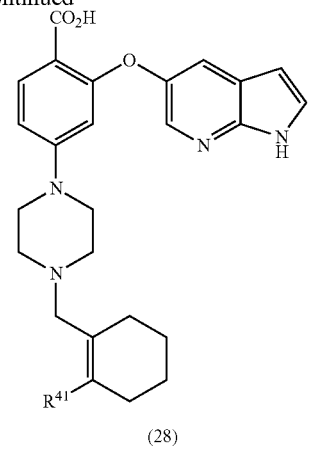

Compounds of Formula (18) can be reacted with mesyl chloride and a base such as but not limited to triethylamine, followed by N-t-butoxycarbonylpiperazine, to provide compounds of Formula (24). Compounds of Formula (25) can be prepared by reacting compounds of Formula (24) with triethylsilane and trifluoroacetic acid. Compounds of Formula (25) can be reacted with compounds of Formula (26) and $HK_2PO_4$ to provide compounds of Formula (27) in a solvent such as but not limited to dimethylsulfoxide. Compounds of Formula (28) can be prepared from compounds of Formula (27) as described in SCHEME 1, and can be used as described in SCHEME 7 to prepare compounds of Formula (I).

SCHEME 7

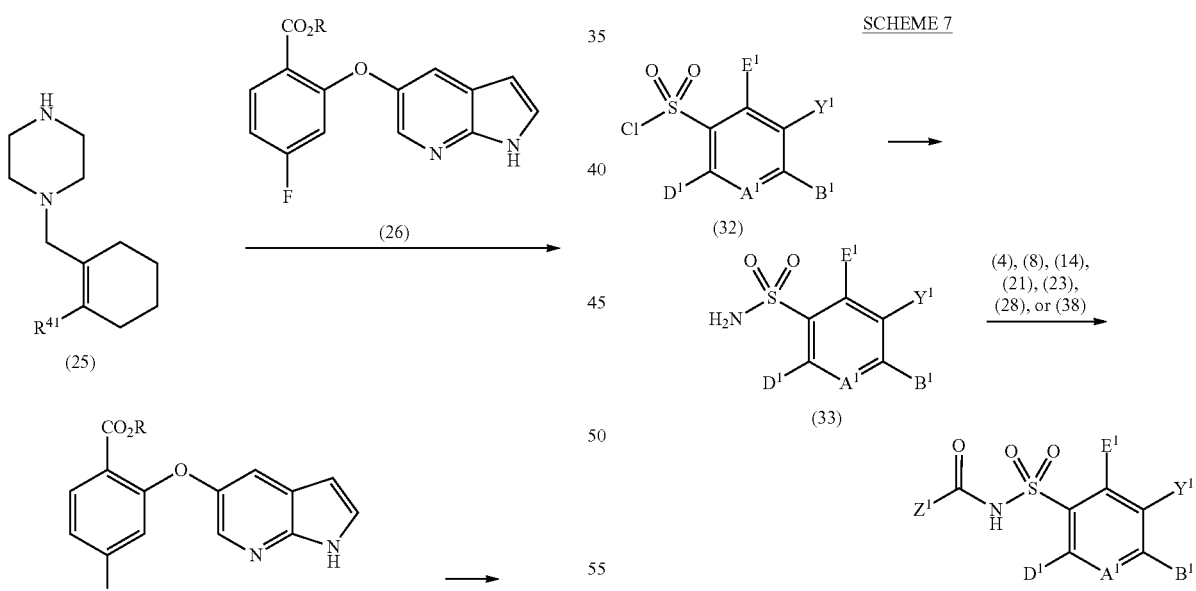

As shown in SCHEME 7, compounds of Formula (32), which can be prepared as described herein, may be converted to compounds of Formula (33) by reacting the former with ammonia. Compounds of Formula (33) may be converted to compounds of Formula (I) by reacting the former and compounds of Formula (4), (8), (14), (21), (23), (28), or (38) and a coupling agent, with or without a first base. Examples of coupling agents include 1-ethyl-3-[3-(dimethylamino)propyl]-carbodiimide hydrochloride, 1,1'-carbonyldiimidazole, and benzotriazol-1-yl-oxytripyrrolidinophosphonium hexafluorophosphate. Examples of first bases include triethylamine, N,N-diisopropylethylamine, 4-(dimethylamino)pyridine, and mixtures thereof

SCHEME 8

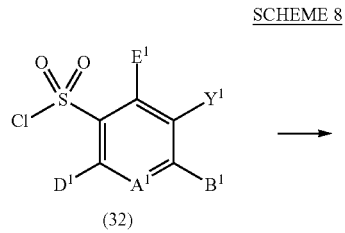

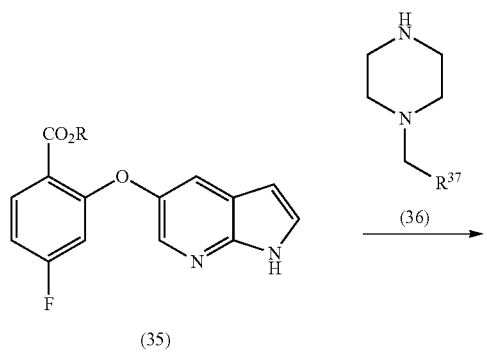

Compounds of Formula (33), prepared as described in SCHEME 7, can also be converted to compounds of Formula (I) by reacting the former and compounds of Formula (34) and a first base. Examples of first bases include but are not limited to sodium hydride, triethylamine, N,N-diisopropylethylamine, 4-(dimethylamino)pyridine, and mixtures thereof

SCHEME 9

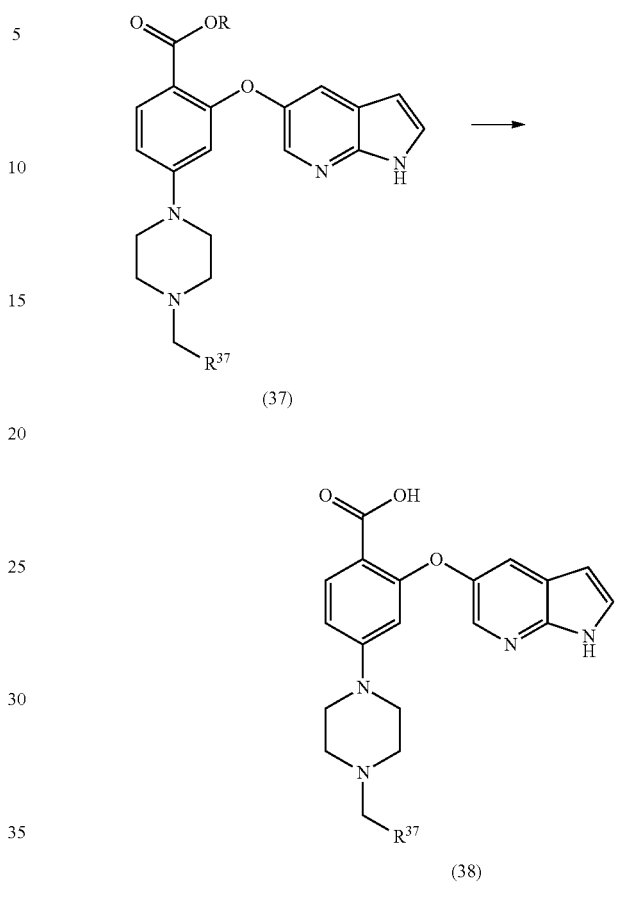

As shown in SCHEME 9, compounds of Formula (35), wherein L is O, can be reacted with compounds of Formula (36), to provide compounds of Formula (37). The reaction is typically performed at elevated temperatures in a solvent such as but not limited to dimethylsulfoxide, and may require the use of a base such as but not limited to potassium phosphate, potassium carbonate, and the like. Compounds of Formula (38) can be prepared from compounds of Formula (37) as described in SCHEME 1, and can be used as described in SCHEME 7 to prepare compounds of Formula (I).

SCHEME 10

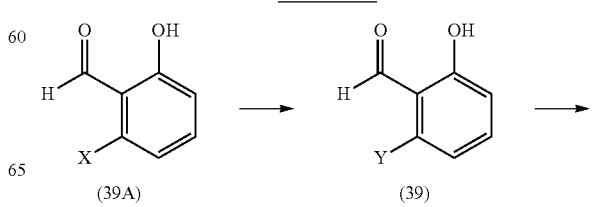

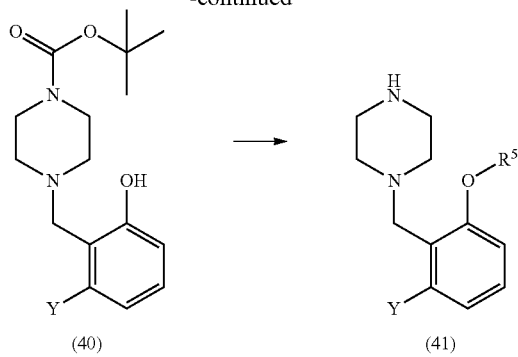

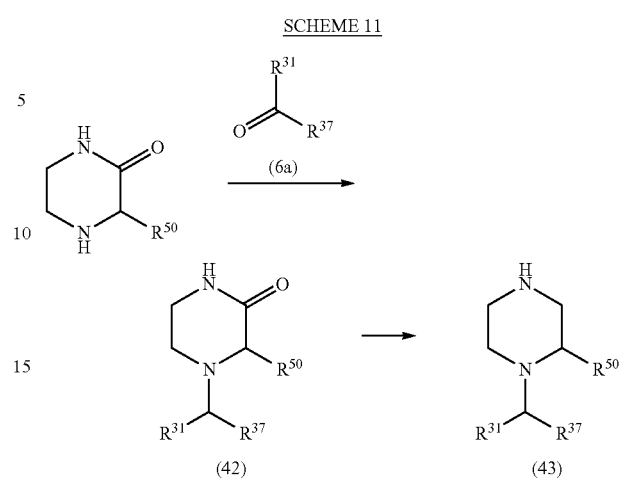

SCHEME 11

Compounds of Formula (39), wherein Y is as described herein for substituents on $R^{37}$, can be prepared from compounds of Formula (39A) wherein X is a halide or triflate, and Y—B(OH)$_2$ using Suzuki coupling conditions known to those skilled in the art and readily available in the literature. Compounds of Formula (39) can be reacted with tert-butyl piperazine-1-carboxylate and a reducing agent such as sodium triacetoxyborohydride to provide compounds of Formula (40). The reaction is typically performed in a solvent such as but not limited to methylene chloride. Compounds of Formula (41) can be prepared from compounds of Formula (40) by reacting the latter with $R^{50}X$, wherein X is a halide, and NaH in a solvent such as N,N-dimethylformamide, and then the resulting material can be treated with triethylsilane and trifluoroacetic acid in dichloromethane. Compounds of Formula (41) can be used as described in Scheme 9 wherein $CH_2R^{37}$ is as shown in Formula (41).

As shown in SCHEME 11, substituted piperazin-2-ones wherein $R^{50}$ is alkyl, can be reacted with compounds of Formula (6a) and a reducing agent such as sodium triacetoxyborohydride in dichloromethane to provide compounds of Formula (42). Compounds of Formula (42) can be reduced to compounds of Formula (43) using a reducing agent such as but not limited to lithium aluminum hydride in a solvent such as but not limited to tetrahydrofuran. Compounds of Formula (43) can be used as described in Scheme 9 wherein $CH_2R^{37}$ is as shown in Formula (43).

SCHEME 12

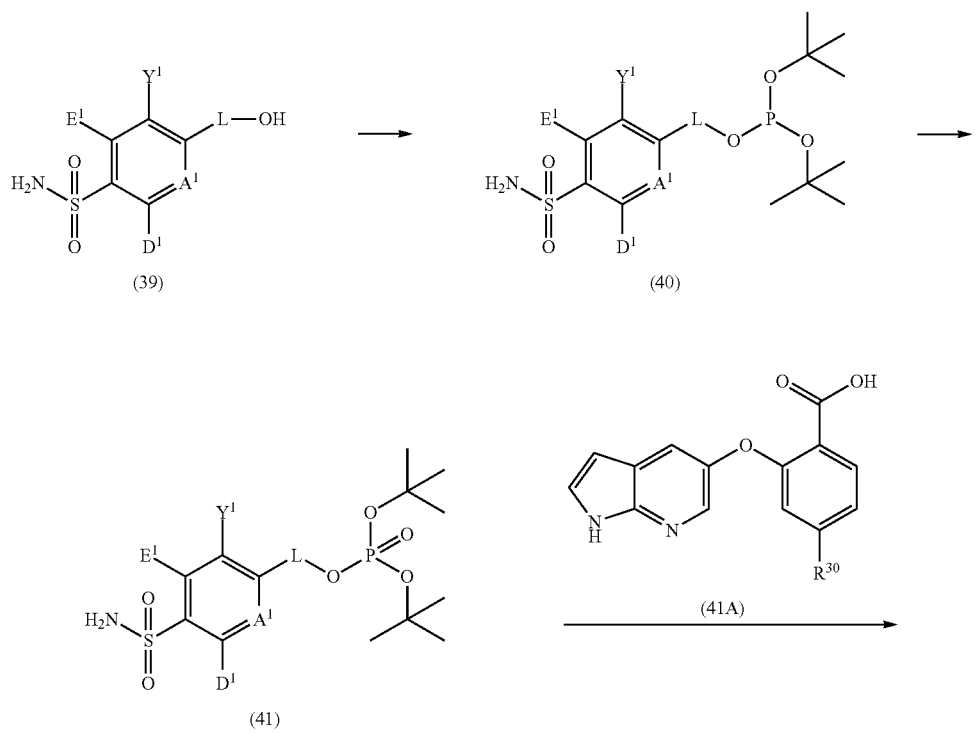

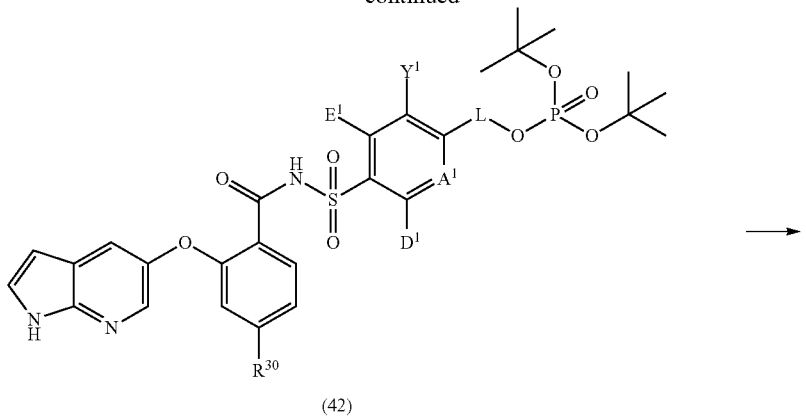

(42)

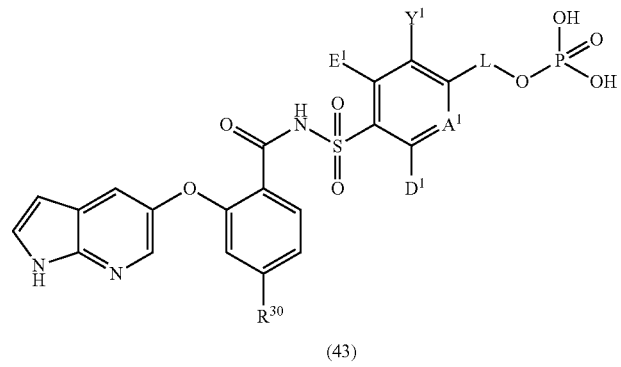

(43)

Compounds of Formula (43), which are representative of compounds of Formula (I), can be prepared as shown in SCHEME 12. Compounds of Formula (39), wherein L is $R^1$, $OR^1$, or $NHR^1$; and $A^1$, $E^1$, $Y^1$, and $D^1$ are as described herein, can be reacted with di-tert-butyl diisopropylphosphoramidite and tetrazole to provide compounds of Formula (40). The reaction is typically performed in a solvent such as but not limited to tetrahydrofuran, at a low temperature before warming to room temperature. Hydrogen peroxide can be added directly to the reaction mixture to provide compounds of Formula (41). The reaction is typically performed at room temperature. Compounds of Formula (41) can be coupled with compounds of Formula (41A), wherein $R^{30}$ is as described herein, using coupling conditions known by those skilled in the art and widely available in the literature to provide compounds of Formula (42). Compounds of Formula (42) can be reacted with an acid, such as but not limited to trifluoroacetic acid, to provide compounds of Formula (43), which are representative of compounds of this invention. The reaction is typically performed in a solvent such as but not limited to dichloromethane.

SCHEME 13

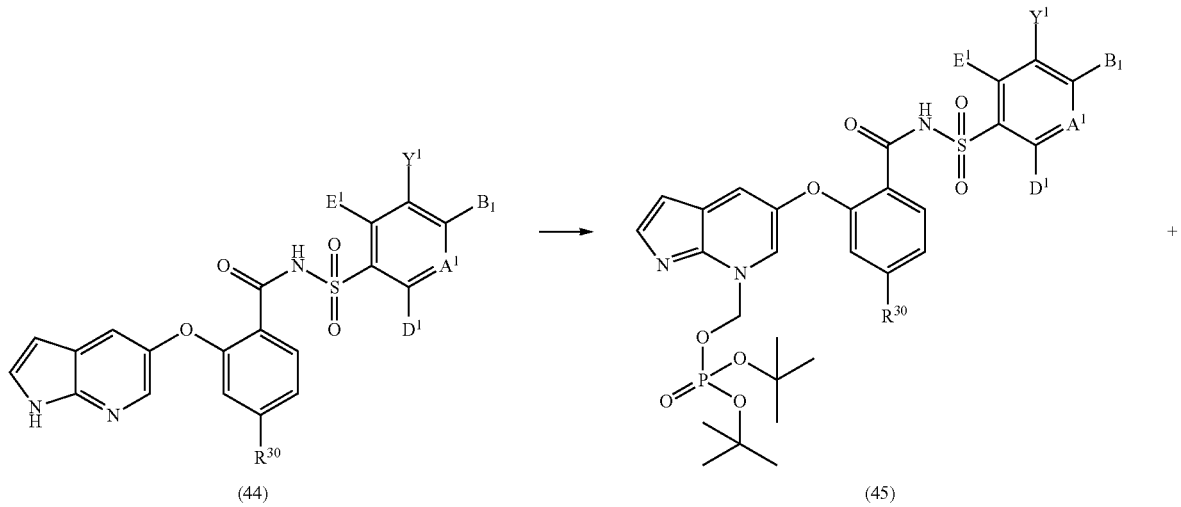

(44) → (45) +

-continued

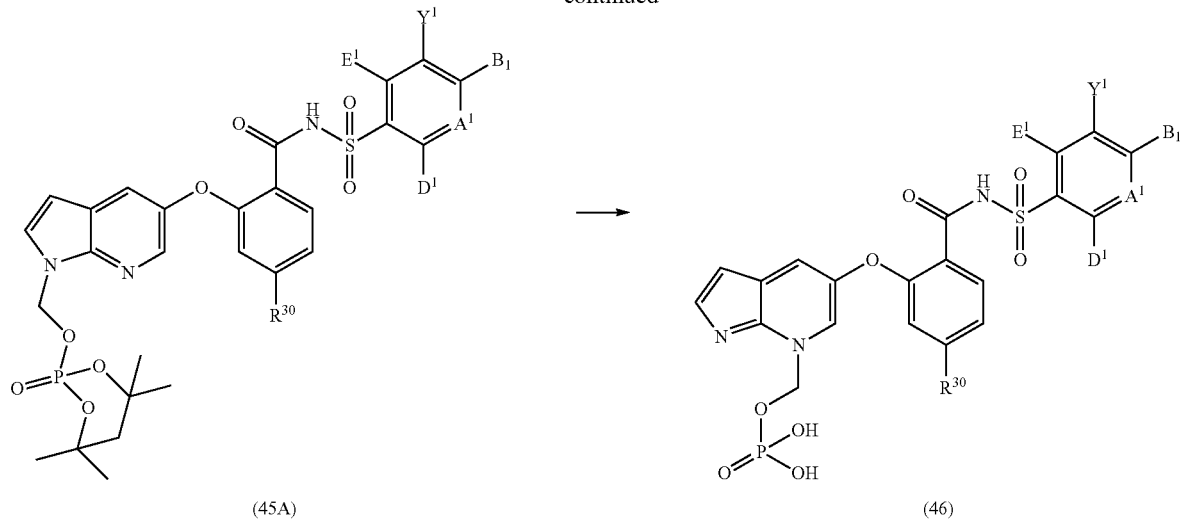

Compounds of Formula (46), which are representative of compounds of Formula (III), can be prepared as shown in SCHEME 13. Compounds of Formula (44), wherein $A^1$, $B^1$, $E^1$, $Y^1$, $D^1$, and $R^{30}$ are as described herein, can be treated with di-tert-butyl chloromethyl phosphate in the presence of a base such as but not limited to N,N-diisopropylethylamine, to provide compounds of Formula (45) and Formula (45A). The reaction is typically performed at elevated temperatures, optionally using a microwave oven, in a solvent such as but not limited to dichloromethane. Compounds of Formula (45) can be reacted with an acid, such as but not limited to trifluoroacetic acid, to provide compounds of Formula (46), which are representative of compounds of this invention. The reaction is typically performed in a solvent such as but not limited to dichloromethane.

The following examples are presented to provide what is believed to be the most useful and readily understood description of procedures and conceptual aspects of this invention. The exemplified compounds were named using ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

EXAMPLE 1

{5-[5-(4-{[2-(4-chlorophenyl)-4,4-dimethylcyclohex-1-en-1-yl]methyl}piperazin-1-yl)-2-{[(4-{[(trans-4-methoxycyclohexyl)methyl]amino}-3-nitrophenyl)sulfonyl]carbamoyl}phenoxy]-7H-pyrrolo[2,3-b]pyridin-7-yl}methyl dihydrogen phosphate

EXAMPLE 1A methyl 4,4-dimethyl-2-(trifluoromethylsulfonyloxy)cyclohex-1-enecarboxylate To a suspension of NaH (pre-washed with hexane 17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoroacetic anhydride (40 mL) was added. The reaction mixture was warmed to room temperature and stirred for 24 hours. The organic layer was washed with brine, dried (Na$_2$SO$_4$), filtered, and concentrated to provide the title compound.

EXAMPLE 1B methyl 2-(4-chlorophenyl)-4,4-dimethylcyclohex-1-enecarboxylate

EXAMPLE 1A (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether (4×200 mL) was added and the mixture was filtered. The combined ether solution was concentrated to give the product.

EXAMPLE 1C (2-(4-chlorophenyl)-4,4-dimethylcyclohex-1-enyl)methanol

To a mixture of LiBH$_4$ (13 g), EXAMPLE 1B (53.8 g) and ether (400 mL), was added methanol (25 mL) slowly by syringe. The mixture was stirred at room temperature for 24 hours. The reaction was quenched with 1N HCl with ice-cooling. The mixture was diluted with water and extracted with ether (3×100 mL). The extracts were dried (Na$_2$SO$_4$), filtered, and concentrated. The residue was purified by flash chromatography, eluting with 0-30% ethyl acetate in hexanes to provide the title compound.

EXAMPLE 1D tert-butyl 4-((2-(4-chlorophenyl)-4,4-dimethylcyclohex-1-enyl)methyl)piperazine-1-carboxylate Methanesulfonyl chloride (7.5 mL) was added via syringe to EXAMPLE 1C (29.3 g) and triethylamine (30 mL) in CH$_2$Cl$_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, (Na$_2$SO$_4$), filtered, and concentrated. The residue was purified by flash chromatography, eluting with 10-20% ethyl acetate in hexanes to provide the title compound.

EXAMPLE 1E 1-((2-(4-chlorophenyl)-4,4-dimethylcyclohex-1-enyl)methyl)piperazine EXAMPLE 1D (200 mg) and triethylsilane (1 mL) were stirred in dichloromethane (15 mL) and trifluoroacetic acid (15 mL) for 1 hour. The mixture was concentrated, taken up in ethyl acetate, washed twice with aqueous $NaH_2PO_4$, and brine, and dried ($Na_2SO_4$), filtered and concentrated to provide the title compound.

EXAMPLE 1F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, triisopropylchlorosilane (18.2 mL) was added. The mixture was stirred at room temperature for 24 hours. The reaction was diluted with ether, and the resulting solution was washed twice with water. The extracts were dried ($Na_2SO_4$), filtered, and concentrated. The residue was purified by flash chromatography, eluting with 10% ethyl acetate in hexanes to provide the title compound.

EXAMPLE 1G 1-(triisopropylsilyl)-1H-pyrrolo[2,3-b]pyridin-5-ol

To a mixture of EXAMPLE 1F (24.3 g) in tetrahydrofuran (500 mL) at −78° C. was added 2.5M BuLi (30.3 mL). After 2 minutes, trimethylborate (11.5 mL) was added, and the mixture was allowed to warm to room temperature over 1 hour. The reaction was poured into water, extracted thee times with ethyl acetate, and the combined extracts were washed with brine and concentrated. The crude product was taken up in tetrahydrofuran (200 mL) at 0° C., and 1M NaOH (69 mL) was added, followed by 30% $H_2O_2$ (8.43 mL), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The residue was purified by flash chromatography, eluting with 5-25% ethyl acetate in hexanes to provide the title compound.

EXAMPLE 1H methyl 2-(1H-pyrrolo[2,3-b]pyridin-5-yloxy)-4-fluorobenzoate

A mixture of EXAMPLE 1G (8.5 g), methyl 2,4-difluorobenzoate (7.05 g), and $K_3PO_4$ (9.32 g) in diglyme (40 mL) at 115° C was stirred for 24 hours. The reaction was cooled, diluted with ether (600 mL), and washed twice with water, and brine, and concentrated. The residue was purified by flash chomatography, eluting with 2-50% ethyl acetate in hexanes to provide the title compound.

EXAMPLE 1I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of EXAMPLE 1H (1.55 g), EXAMPLE 1E (2.42 g), and $HK_2PO_4$ (1.42 g) in dimethylsulfoxide (20 mL) at 135 C. was stirred for 24 hours. The reaction was cooled, diluted with ether (400 mL), and washed three times with 1M aqueous NaOH, and brine, and concentrated. The residue was purified by flash chromatography, eluting with 10-50% ethyl acetate in hexanes to provide the title compound.

EXAMPLE 1J 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid EXAMPLE 1I (200 mg) in dioxane (10 mL) and 1M NaOH (6 mL) at 50° C. was stirred for 24 hours. The reaction was cooled, added to aqueous $NaH_2PO_4$ solution, and extracted three times with ethyl acetate. The combined extracts were washed with brine, and concentrated to give the title product.

EXAMPLE 1K (4-methoxycyclohexyl)methanamine (4-Methoxyphenyl)methanamine (1.0 g) in ethanol (10 ml) was treated with 5% Rh—$Al_2O_3$ (99.8 mg, 0.048 mmol) under $H_2$ atmosphere (500 psi) at 50° C. for 16 hours. Additional 5% Rh—$Al_2O_3$ (0.4 g) was added. The resulting mixture was stirred under $H_2$ atmosphere (500 psi) at 60° C. for 2 hours. The insoluble material was filtered off and the filtrate was concentrated to provide a mixture of cis and trans product as an oil, which was used in the next step without further purification.

EXAMPLE 1L

Trans-4-((4-methoxycyclohexyl)methylamino)-3-nitrobenzenesulfonamide

4-Fluoro-3-nitrobenzenesulfonamide (1.098 g) and EXAMPLE 1K (1 g) in tetrahydrofuran (20 mL) was treated with N,N-diisopropylethylamine (0.871 mL) overnight. The reaction mixture was concentrated and the residue was purified by reverse phase chromatography, eluting with 40-55% acetonitrile in 0.1% trifluoroacetic acid in water over 25 minutes.

EXAMPLE 1M

Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide A mixture of EXAMPLE 1L (35 mg), EXAMPLE 1J (53 mg), 4-dimethylaminopyridine (46 mg) and 1-ethyl-3-[3-(dimethylamino)propyl]-carbodiimide hydrochloride (21.5 mg) in dichloromethane was stirred overnight and concentrated. The residue was purified by reverse phase HPLC, eluting with 40% -70% acetonitrile in 0.1% trifluoroacetic acid water over 40 minutes. The desired fractions were concentrated to remove acetonitrile, neutralized with NaHCO$_3$ and extracted with dichloromethane. The organic layer was dried over Na$_2$SO$_4$, filtered, concentrated and dried to provide the title compound. $^1$H NMR (500 MHz, dimethylsulfoxide-d$_6$) δ 11.69 (s, 1H), 11.37 (s, 1 H), 8.52-8.62 (m, 2 H), 8.04 (d, 1 H), 7.79 (dd, 1 H), 7.47-7.55 (m, 3 H), 7.34 (d, 2 H), 7.02-7.09 (m, 3 H), 6.68 (dd, 1 H), 6.39 (dd, 1 H), 6.19 (d, 1 H), 3.21-3.27 (m, 5 H), 3.02-3.12 (m, 5 H), 2.75 (s, 2 H), 2.20 (s, 4 H), 2.14 (s, 2 H), 1.93-2.04 (m, 4 H), 1.79 (d, 2 H), 1.55-1.65 (m, 1 H), 1.38 (t, 2 H), 0.97-1.12 (m, 4 H), 0.92 (s, 6 H).

EXAMPLE 1N

{5-[5-(4-{[2-(4-chlorophenyl)-4,4-dimethylcyclohex-1-en-1-yl]methyl}piperazin-1-yl)-2-{[(4-{[(trans-4-methoxycyclohexyl)methyl]amino}-3-nitrophenyl)sulfonyl]carbamoyl}phenoxy]-7H-pyrrolo[2,3-b]pyridin-7-yl}methyl dihydrogen phosphate To a solution of EXAMPLE 1M (1.2 g) in acetonitrile (20 mL) was added di-tert-butyl chloromethyl phosphate (1.1 g) and N,N-diisopropylethylamine (1.2 mL). The mixture was heated in a Biotage microwave synthesizer at 80° C. for 1.5 hours and concentrated. The residue was dissolved in dichloromethane (5 ml), treated with trifluoroacetic acid (5 ml) for 1 hour and concentrated. The residue was purified by reverse phase chromatography, and was eluted with 40%-65% acetonitrile in 0.1% trifluoroacetic acid water to give the title compound as a trifluoroacetic acid salt. $^1$H NMR (300 MHz, DMSO-d$_6$) δ ppm 8.73 (d, 1 H), 8.60 (t, 1 H), 8.53 (d, 1 H), 8.46 (d, 1 H), 7.98 (d, 1 H), 7.81 (dd, 1 H), 7.57 (d, 1 H), 7.40 (d, 2 H), 7.15 (d, 1 H), 7.09 (d, 2 H), 6.85 (d, 1 H), 6.46 (d, 1 H), 6.25 (d, 2 H), 3.28 (m, 4 H), 3.22 (s, 3 H), 3.03 (m, 3 H), 2.25 (m, 3 H), 2.01 (m, 5 H), 1.78 (m, 3 H), 1.61 (m, 2 H), 1.46 (m, 4 H), 1.03 (m, 6 H), 0.95 (s, 6 H).

EXAMPLE 2

(5-{5-(4-{[2-(4-chlorophenyl)-4,4-dimethylcyclohex-1-en-1-yl]methyl}piperazin-1-yl)-2[({3-nitro-4-[(tetrahydro-2H-pyran-4-ylmethyl)amino]phenyl}sulfonyl)carbamoyl]phenoxy}-7H-pyrrolo[2,3-b]pyridin-7-yl)methyl dihydrogen phosphate

EXAMPLE 2A 3-nitro-4-((tetrahydro-2H-pyran-4-yl)methylamino)benzenesulfonamide A mixture of 4-fluoro-3-nitrobenzenesulfonamide (2.18 g), 1-(tetrahydropyran-4-yl)methylamine (1.14 g), and triethylamine (1 g) in tetrahydrofuran (30 mL) were stirred overnight, neutralized with concentrated HCl and concentrated. The residue was suspended in ethyl acetate and the precipitates were collected, washed with water and dried to provide the title compound.

EXAMPLE 2B 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide EXAMPLE 1J (3.39 g), EXAMPLE 2A (1.87 g), 1-ethyl-3-[3-(dimethylamino)propyl]-carbodiimide hydrochloride (2.39 g), and 4-dimethylaminopyridine (1.09 g) were stirred in CH$_2$Cl$_2$ (40 mL) for 24 hours. The residue was purified by flash chromatography, eluting with 25-100% ethyl acetate in hexanes, then 10% methanol in ethyl acetate with 1% acetic acid to give the product as a white solid. $^1$H NMR (300 MHz, dimethylsulfoxide-d$_6$) 11.65 (brs, 1H), 8.55 (br s, 1H), 8.04 (d, 1H), 7.89 (dd, 1H), 7.51 (m, 3H), 7.33 (d, 2H), 7.08 (m, 1H), 7.04 (d, 2H), 6.68 (dd, 1H), 6.39 (d, 1H), 6.19 (d, 1H), 3.84 (m, 1H), 3.30 (m, 4H), 3.07 (m, 4H), 2.73(m, 2H), 2.18 (m, 6H), 1.95 (m, 2H), 1.61 (dd, 2H), 1.38 (m, 2H), 1.24 (m, 4H), 0.92 (s, 6H).

EXAMPLE 2C (5-{5-(4-{[2-(4-chlorophenyl)-4,4-dimethylcyclohex-1-en-1-yl]methyl}piperazin-1-yl)-2-[({3-nitro-4-[(tetrahydro-2H-pyran-4-ylmethyl)amino]phenyl}sulfonyl)carbamoyl]phenoxy}-7H-pyrrolo[2,3-b]pyridin-7-yl)methyl dihydrogen phosphate The title compound was prepared according to the procedure described in EXAMPLE 1N by substituting EXAMPLE 1M with EXAMPLE 2B. $^1$H NMR (300 MHz, DMSO-D$_6$) δ ppm 8.72 (d, 1 H), 8.61 (t, 1 H), 8.53 (t, 1 H), 8.46 (d, 1 H), 7.98 (d, 1 H), 7.82 (dd, 1 H), 7.57 (d, 1 H), 7.39 (d, 2 H), 7.19 (d, 1 H), 7.09 (d, 2 H), 6.84 (d, 1 H), 6.79 (dd, 1 H), 6.46 (d, 1 H), 6.25 (d, 2 H), 3.85 (m, 6 H), 3.29 (m, 8 H), 2.23 (m, 3 H), 2.03 (s, 3 H), 1.89 (m, 2 H), 1.62 (m, 3 H), 1.46 (t, 2 H), 1.27 (m, 3 H), 0.95 (s, 6 H).

EXAMPLE 3

(5-{5-(4-{[2-(4-chlorophenyl)-4,4-dimethylcyclohex-1-en-1-yl]methyl}piperazin-1-yl)-2-[({4-[(4-fluorotetrahydro-2H-pyran-4-yl)methoxy]-3-nitrophenyl}sulfonyl)carbamoyl]phenoxy}-7H-pyrrolo[2,3-b]pyridin-7-yl)methyl dihydrogen phosphate

EXAMPLE 3A 1,6-dioxaspiro[2.5]octane-2-carbonitrile

A mixture of tetrahydropyran-4-one (10 mL) and chloroacetonitrile (6.4 mL) in tert-butanol (10 mL) was stirred for 10 minutes. To this solution was added a solution of potassium tert-butoxide (12.11 g) in 200 mL of tert-butanol at room temperature over 40 minutes. The reaction mixture was stirred for 16 hours, diluted with water and quenched slowly with 1 N aqueous HCl. The solvent was partially removed by rotary evaporation. It was then extracted with ether (5×200 mL). The combined extracts was washed with brine, dried over MgSO$_4$, filtered, and the filtrate was concentrated and purified by flash chomatography on silica with 3:7 to 1:1 ethyl acetate:hexanes to provide the title compound.

EXAMPLE 3B 2-(4-fluorotetrahydro-2H-pyran-4-yl)-2-hydroxyacetonitrile

EXAMPLE 3A (11.5 g) in dichloromethane (40 mL) in a polypropylene bottle was treated with 70% hydrogen fluoride-pyridine (10.4 mL) dropwise at 0° C. The solution was allowed to warm to room temperature over 3 hours, and stirred for an additional 1.5 hours. The reaction mixture was diluted with ethyl acetate (200 mL) and poured into saturated aqueous NaHCO₃. Additional solid NaHCO₃ was used carefully until bubbling ceased. The organic layer was isolated, and the aqueous layer was extracted with additional ethyl acetate three times (150 mL each). The combined organic layers were washed with 5% HCl (50 mL each, twice), brine, dried over MgSO₄, filtered and concentrated to give the desired product which was used directly in the next step.

EXAMPLE 3C (4-fluorotetrahydro-2H-pyran-4-yl)methanol

EXAMPLE 3B (11.7 g, 74 mmol) in 2-propanol (150 mL) and water (37.5 mL) was cooled to 0° C. To this solution was added NaBH₄ (4.20 g, 111 mmol). The solution was stirred and allowed to warm to room temperature over 3 hours. It was quenched with acetone, and stirred for another 1 hour. The clear liquid was separated from solid by decanting. Additional ethyl acetate (2×100 mL) was used to wash the solid, and the mixture was decanted. The combined organic solutions were concentrated. The residue was purified by flash chomatography, eluting with 1:1 ethyl acetate:hexanes to provide the title compound.

EXAMPLE 3D 4-((4-fluorotetrahydro-2H-pyran-4-yl)methoxy)-3-nitrobenzenesulfonamide EXAMPLE 3C (2.0 g) and 4-fluoro-3-nitrobenzenesulfonamide (2.84 g) in tetrahydrofuran (30 mL) was treated with 60% NaH (1.377 g) overnight. The mixture was poured into water, neutralized with 10% HCl, and extracted with ethyl acetate thee times. The combined organic layers were washed with brine, dried over MgSO₄, filtered, and concentrated. The residue was triturated with a mixture of ethyl acetate and hexane to provide the title compound.

EXAMPLE 3E 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide The title compound was prepared according to the procedures described in EXAMPLE 1M by substituting EXAMPLE 1L with EXAMPLE 3D. ¹H NMR (dimethylsulfoxide-d₆). 11.64 (s, 2H), 8.33 (s, 1H), 8.00-8.01 (m, 2H), 7.39-7.57 (m, 4H), 7.33 (d, J=8.24 Hz, 2H), 7.03 (d, J=8/54 Hz, 2H), 6.65 (dd, J=9, 1.98 Hz, 1H), 6.37-6.38 (m, 1H), 6.19 (d, J=1.53 Hz, 1H), 4.35 (d, J=20.75 Hz, 2H), 3.74-3.78 (m, 2H), 3.55-3.60 (m, 2H), 3.07 (br, 4H), 2.80 (br, 2H), 2.25 (br, 4H), 2.13 (br, 2H), 1.81-1.94 (m, 6H), 1.38 (t, J=6.26 Hz, 2H), 0.91 (s, 6H).

EXAMPLE 3F (5-{5-(4-{[2-(4-chlorophenyl)-4,4-dimethylcyclohex-1-en-1-yl]methyl}piperazin-1-yl)-2-[({4-[(4-fluorotetrahydro-2H-pyran-4-yl)methoxy]-3-nitrophenyl}sulfonyl)carbamoyl]phenoxy}-7H-pyrrolo[2,3-b]pyridin-7-yl)methyl dihydrogen phosphate The title compound was prepared according to the procedures described in EXAMPLE 1N by substituting EXAMPLE 1M with EXAMPLE 3E. ¹H NMR (300 MHz, DMSO-d₆) δ ppm 8.72 (d, 1 H), 8.43 (d, 1 H), 8.36 (d, 1 H), 8.09 (dd, 1 H), 7.95 (d, 1 H), 7.59 (d, 1 H), 7.53 (d, 1 H), 7.40 (d, 2 H), 7.09 (d, 2 H), 6.84 (d, 1 H), 6.80 (dd, 1 H), 6.49 (d, 1 H), 6.25 (d, 2 H), 4.42 (d, 3 H), 3.79 (m, 6 H), 2.21 (m, 3 H), 2.03 (s, 3 H), 1.85 (m, 6 H), 1.46 (t, 2 H), 0.95 (s, 6 H).

EXAMPLE 4

3-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]-2,2-dimethylpropyl dihydrogen phosphate

EXAMPLE 4A 4-(3-hydroxy-2,2-dimethylpropylamino)-3-nitrobenzenesulfonamide

The title compound was prepared as described in EXAMPLE 2A using 3-amino-2,2-dimethylpropan-1-ol in place of (tetrahydro-2H-pyran-4-yl)methanamine.

EXAMPLE 4B di-tert-butyl 2,2-dimethyl-3-(2-nitro-4-sulfamoylphenylamino)propyl phosphate To a solution of EXAMPLE 4A (540 mg) in tetrahydrofuran (5 ml) was added di-tert-butyl diisopropylphosphoramidite (0.84 ml) and 0.45 M 1H-tetrazole (7.91 ml) at 0° C. The mixture was stirred at room temperature for 1.5 hours and cooled to 0° C. 30% Hydrogen peroxide (0.82 ml) was added. The mixture was stirred at room temperature for 30 minutes. Ice water and sodium bissulfite (1.1 g) were added. The resulting mixture was diluted with dichloromethane and the organic layer was washed with water extensively until the water layer became pH neutral. The organic layer was dried over Na₂SO₄, filtered and concentrated. The residue was purified by flash chromatography, eluting with 0-66% ethyl acetate in dichloromethane to provide the title compound.

EXAMPLE 4C 3-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)-2,2-dimethylpropyl di-tert-butyl phosphate The title compound was prepared as described in EXAMPLE 1M using EXAMPLE 4B in place of EXAMPLE 1L.

EXAMPLE 4D

3-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]-2,2-dimethylpropyl dihydrogen phosphate EXAMPLE 4C (250 mg) in dichloromethane (25 ml) at 0° C. was treated with trifluoroacetic acid (4 ml). The mixture was stirred at 0° C. for 30 minutes and at room temperature for 1 hour and concentrated. The residue was dissolved in acetonitrile and saturated NaHCO$_3$ was added until pH 9, followed by the addition of saturated Na$_2$CO$_3$ (0.5 ml). The mixture was concentrated, and the residue was purified by HPLC, and eluted with 30% -70% methanol in water to provide the title compound.

$^1$H NMR (400 MHz, DMSO-d$_6$) δ ppm 8.41 (s, 1 H), 8.21 (s, 1 H), 7.83 (d, 1 H), 7.52 (d, 1 H), 7.25-7.42 (m, 4 H), 6.89-7.09 (m, 4 H), 6.64 (s, 1 H), 6.29 (d, 1 H), 6.08 (d, 1 H), 2.91-3.12 (m, 6 H), 2.68-2.79 (m, 2 H), 2.06-2.26 (m, 6 H), 1.88-1.99 (m, 2 H), 1.37 (s, 2 H), 0.67-0.98 (m, 12 H).

EXAMPLE 5

Trans-4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenoxy)methyl]cyclohexyl dihydrogen phosphate

EXAMPLE 5A

Trans-4-(4-(tert-butyldimethylsilyloxy)cyclohexyl)methoxy)-3-nitrobenzenesulfonamide The title compound was prepared as described in EXAMPLE 3D by replacing EXAMPLE 3C with trans-(4-(tert-butyldimethylsilyloxy)cyclohexyl)methanol (made according to the procedures in WO 2008/124878).

EXAMPLE 5B 4-((trans-4-hydroxycyclohexyl)methoxy)-3-nitrobenzenesulfonamide

A solution of EXAMPLE 5A (630 mg) in methanol (5 ml) and dichloromethane (5 ml) was treated with concentrated HCl (1.5 ml) for 1 hour and the mixture was concentrated. The residue was dried under vacuum to provide the title compound.

EXAMPLE 5C

Di-tert-butyl trans-4-((2-nitro-4-sulfamoylphenoxy)methyl)cyclohexyl phosphate

The title compound was prepared as described in EXAMPLE 4B using EXAMPLE 5B in place of EXAMPLE 4A.

EXAMPLE 5D

Trans-4-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenoxy)methyl)cyclohexyl di-tert-butyl phosphate The title compound was prepared as described in EXAMPLE 1M using EXAMPLE 5C in place of EXAMPLE 1L.

EXAMPLE 5E

Trans-4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenoxy)methyl]cyclohexyl dihydrogen phosphate The title compound was prepared as described in EXAMPLE 4D using EXAMPLE 5D in place of EXAMPLE 4C. $^1$H NMR (400 MHz, DMSO-d$_6$) δ ppm 11.61 (s, 1 H), 8.09 (s, 1 H), 7.90 (s, 1 H), 7.65-7.80 (m, 1 H), 7.59 (d, 1 H), 7.20-7.41 (m, 4 H), 6.97-7.08 (m, 3 H), 6.49-6.66 (m, 1 H), 6.21-6.30 (m, 2 H), 3.73-3.97 (m, 2 H), 2.98 (s, 4 H), 2.69 (d, 2 H), 2.14 (s, 7 H), 1.94 (s, 2 H), 1.57-1.81 (m, 3 H), 1.37 (s, 2 H), 1.11 (d, 4 H), 0.91 (s, 6 H).

EXAMPLE 6

4-(4-{[2-(4-chlorophenyl)-4,4-dimethylcyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide The title compound was prepared as described in EXAMPLE 1M using EXAMPLE 4A in place of EXAMPLE 1L. $^1$H NMR (500 MHz, dimethylsulfoxide-d$_6$) δ 11.68 (s, 1H), 11.35 (s, 1H), 8.96 (t, 1H), 8.56 (d, 1H), 8.05 (d, 1H), 7.79 (dd, 1H), 7.46-7.56 (m, 3H), 7.34 (d, 2H), 7.10 (d, 1H), 7.04 (d, 2H), 6.68 (dd, 1H), 6.39 (dd, 1H), 6.19 (d, 1H), 5.10 (t, 1H), 3.29 (d, 1H), 3.24 (d, 1H), 3.07 (s, 4H), 2.75 (s, 2H), 2.17 (d, 6H), 1.95 (s, 2H), 1.38 (t, 2H), 0.93 (d, 12H).

EXAMPLE 7

Trans-4-(4-{[2-(4-chlorophenyl)-4,4-dimethylcyclohex-1-en-1-yl]methyl}piperazin-1-yl)-N-({4-[4-hydroxycyclohexyl)methoxy]-3-nitrophenyl}sulfonyl)-2-(1H-pyrrolo[2,3-b]pyridin-5-yloxy)benzamide The title compound was prepared as described in EXAMPLE 1M using EXAMPLE 5B in place of EXAMPLE 1L. $^1$H NMR (400 MHz, dimethylsulfoxide-d$_6$) δ 11.69 (s, 1H), 11.27 (s, 1H), 8.34 (d, 1H), 7.95-8.08 (m, 2H), 7.47-7.55 (m, 3H), 7.32-7.40 (m, 3H), 7.01-7.07 (m, 2H), 6.68 (dd, 1H), 6.39 (dd, 1H), 6.20 (d, 1H), 4.54 (d, 1H), 3.96-4.06 (m, 2H), 3.10 (s, 4H), 2.84 (s, 2H), 2.05-2.39 (m, 6H), 1.96 (s, 2H), 1.46-1.93 (m, 5H), 1.39 (t, 2H), 0.98-1.29 (m, 4H), 0.92 (s, 6H).

What is claimed is:

1. A compound having Formula (IIIa):

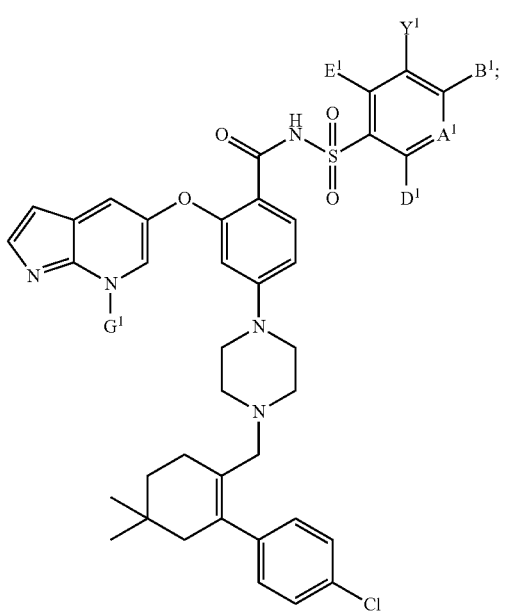

(IIIa)

or a therapeutically acceptable salt thereof, wherein
$A^1$ is $C(A^2)$;
$A^2$ is H;
$B^1$ is $OR^1$, or $NHR^1$, wherein $R^1$ is alkyl substituted with $R^{10}$;
$D^1$ is H;
$E^1$ is H;
$Y^1$ is $NO_2$;
$G^1$ is alkyl substituted with $OP(O)(OH)(OH)$;

$R^{10}$ $C_3$-$C_{10}$-cycloalkyl, each having one or two $CH_2$ moieties unreplaced or replaced with independently selected O;
wherein the moiety represented by $R^{10}$ is unsubstituted or substituted with one or two or three or four or five substituents independently selected from the group consisting of $R^{50}$, $OR^{50}$, F, Cl, Br, and I; and
$R^{50}$ is alkyl.

2. The compound or therapeutically acceptable salt of claim 1, wherein the compound is selected from the group consisting of:

(5- {5-(4- {[2-(4-chlorophenyl)-4,4-dimethylcyclohex-1-en-1-yl]methyl}piperazin-1-yl)-2-[({3-nitro-4-[(tetrahydro-2H-pyran-4-ylmethyl)amino]phenyl}sulfonyl)carbamoyl]phenoxy}-7H-pyrrolo[2,3-b]pyridin-7-yl)methyl dihydrogen phosphate;

{5-[5-(4-{[2-(4-chlorophenyl)-4,4-dimethylcyclohex-1-en-1-yl]methyl}piperazin-1-yl)-2-{[(4-{[(trans-4-methoxycyclohexyl)methyl]amino }-3-nitrophenyl)sulfonyl]carbamoyl}phenoxy]-7H-pyrrolo[2,3-b]pyridin-7-yl }methyl dihydrogen phosphate; and (5-{5-(4-{[2-(4-chlorophenyl)-4,4-dimethylcyclohex-1-en-1-yl]methyl}piperazin-1-yl)-2-[({4- [(4-fluorotetrahydro-2H-pyran-4-yl)methoxy]-3-nitrophenyl}sulfonyl)carbamoyl]phenoxy}-7H-pyrrolo[2,3-b]pyridin-7-yl)methyl dihydrogen phosphate.

3. A pharmaceutical composition comprising the compound or therapeutically acceptable salt of claim 1 and an excipient.

4. A pharmaceutical composition comprising the compound or therapeutically acceptable salt of claim 2 and an excipient.

5. A method for inhibiting anti-apoptotic Bcl-2 protein function in a cell comprising contacting a cell comprising anti-apoptotic Bcl-2 protein with the compound or therapeutically acceptable salt of any one of claims 1 and 2.

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: F-Bak Probe Peptide
<220> FEATURE:
<221> NAME/KEY: MOD_RES
<222> LOCATION: 1
```

```
<223> OTHER INFORMATION: Gly is modified with acetyl
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
 1               5                   10                  15
```